US012752048B2

(12) United States Patent
Askem et al.

(10) Patent No.: US 12,752,048 B2
(45) Date of Patent: Oct. 6, 2026

(54) CANISTER STATUS DETERMINATION FOR NEGATIVE PRESSURE WOUND THERAPY DEVICES

(71) Applicant: T.J.Smith and Nephew,Limited, Hull (GB)

(72) Inventors: Ben Alan Askem, Leeds (GB); David Michael Elder, Hull (GB); Robert Gregory, East Yorkshire (GB); David Garcia Guardiola, Valencia (ES); Allan Kenneth Frazer Grugeon Hunt, Beverley (GB); Andrea Maggiore, Hull (GB); Christopher James Milner, Hedon (GB); Felix Clarence Quintanar, Hull (GB); Kirsty Margaret Strachan, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 79 days.

(21) Appl. No.: 18/283,918

(22) PCT Filed: Apr. 20, 2022

(86) PCT No.: PCT/EP2022/060463
§ 371 (c)(1),
(2) Date: Sep. 25, 2023

(87) PCT Pub. No.: WO2022/223645
PCT Pub. Date: Oct. 27, 2022

(65) Prior Publication Data

US 2024/0165318 A1 May 23, 2024

(30) Foreign Application Priority Data

Apr. 21, 2021 (EP) .................................... 21382346

(51) Int. Cl.
*A61M 1/00* (2006.01)

(52) U.S. Cl.
CPC ....... *A61M 1/98* (2021.05); *A61M 2205/3331* (2013.01)

(58) Field of Classification Search
CPC ............ A61M 1/98; A61M 2205/3331; A61M 1/982; A61M 2205/18; A61M 2205/3317;
(Continued)

(56) References Cited

U.S. PATENT DOCUMENTS

| | | | |
|---|---|---|---|
| 730,062 | A | 6/1903 | Widmer |
| 2,468,445 | A | 4/1949 | Kenneth et al. |

(Continued)

FOREIGN PATENT DOCUMENTS

| | | | |
|---|---|---|---|
| CN | 2623320 | Y | 7/2004 |
| DE | 4312852 | A1 | 10/1993 |

(Continued)

OTHER PUBLICATIONS

Fong K.D., et al., "SNaP Wound Care System: Ultraportable Mechanically Powered Negative Pressure Wound Therapy," Advances in Wound Care, vol. 1(1), Feb. 2012, 4 pages.

(Continued)

*Primary Examiner* — Guy K Townsend
*Assistant Examiner* — Alessandro R Del Priore
(74) *Attorney, Agent, or Firm* — Knobbe, Martens, Olson & Bear, LLP

(57) ABSTRACT

A negative pressure wound therapy device can include one or more fluid detection systems. A canister fluid level detection system can incorporate various fluid detection devices to communicate data relating to the fluid level of the canister. In some cases, a negative pressure wound therapy device can include a device housing, a negative pressure source, and a canister configured to be in fluid communication with the negative pressure source. The canister can include a canister housing configured to store fluid aspirated (Continued)

from a wound, a cap connected to the canister housing, and a fluid level sensor supported by the cap. The fluid level sensor can be configured to detect a completed electrical circuit when the fluid aspirated from the wound comes into contact with the sensor. An electronic circuitry can be configured to detect a state of the sensor and provide an indication of a status of the canister.

6 Claims, 19 Drawing Sheets

(58) Field of Classification Search
CPC .. A61M 2205/3382; A61M 2205/3569; A61M 1/90; A61M 1/60; A61M 27/00
See application file for complete search history.

(56) References Cited

U.S. PATENT DOCUMENTS 3,980,166 A 9/1976 De Feudis
4,063,556 A 12/1977 Thomas et al.
4,136,696 A 1/1979 Nehring
4,203,445 A 5/1980 Jessup et al.
4,228,798 A 10/1980 Deaton
4,266,545 A 5/1981 Moss
4,293,609 A 10/1981 Erickson
4,321,020 A 3/1982 Mittal
4,331,147 A 5/1982 Armstrong
4,569,674 A 2/1986 Phillips et al.
4,578,060 A 3/1986 Huck et al.
4,585,397 A 4/1986 Crawford et al.
4,604,313 A 8/1986 McFarland et al.
4,758,238 A 7/1988 Sundblom et al.
4,767,417 A 8/1988 Boehringer et al.
4,826,494 A 5/1989 Richmond et al.
4,865,816 A 9/1989 Walz et al.
4,870,975 A 10/1989 Cronk et al.
4,979,944 A 12/1990 Luzsicza
4,988,344 A 1/1991 Reising et al.
4,988,345 A 1/1991 Reising
5,071,104 A 12/1991 Witt et al.
5,135,485 A 8/1992 Cohen et al.
5,141,504 A 8/1992 Herweck et al.
5,156,602 A 10/1992 Steffler
5,246,353 A 9/1993 Sohn
D352,463 S 11/1994 Kubo
5,360,445 A 11/1994 Goldowsky
5,386,735 A 2/1995 Langdon
5,397,299 A 3/1995 Karwoski et al.
5,411,474 A 5/1995 Ott et al.
5,458,586 A 10/1995 Adiletta
5,466,229 A 11/1995 Elson et al.
5,484,428 A 1/1996 Drainville et al.
5,591,297 A 1/1997 Ahr
5,630,855 A 5/1997 Lundb ack
5,685,214 A 11/1997 Neff et al.
5,707,173 A 1/1998 Cottone et al.
5,785,700 A 7/1998 Olson
5,787,928 A 8/1998 Allen et al.
5,807,359 A 9/1998 Bemis et al.
D400,249 S 10/1998 Holubar
5,876,387 A 3/1999 Killian et al.
5,882,743 A 3/1999 McConnell
5,960,837 A 10/1999 Cude
6,010,527 A 1/2000 Augustine et al.
6,075,177 A 6/2000 Bahia et al.
6,099,493 A 8/2000 Swisher
6,102,205 A 8/2000 Greff et al.
6,168,758 B1 1/2001 Forsberg et al.
D449,891 S 10/2001 Moro
6,352,233 B1 3/2002 Barberich
D456,514 S 4/2002 Brown et al.
6,395,955 B1 5/2002 Roe et al.
6,458,109 B1 10/2002 Henley et al.
6,468,199 B1 10/2002 Satou et al.
6,501,002 B1 12/2002 Roe et al.
6,547,255 B1 4/2003 Donaway et al.
D475,132 S 5/2003 Randolph
6,575,333 B1 6/2003 Raboin
D477,869 S 7/2003 Vijfvinkel
D478,659 S 8/2003 Hall et al.
6,620,379 B1 9/2003 Piuk et al.
D481,459 S 10/2003 Nahm
6,723,430 B2 4/2004 Kurata et al.
6,755,807 B2 6/2004 Risk, Jr. et al.
6,764,462 B2 7/2004 Risk, Jr. et al.
6,800,074 B2 10/2004 Henley et al.
6,820,483 B1 11/2004 Beckerman
6,856,821 B2 2/2005 Johnson
6,885,116 B2 4/2005 Knirck et al.
D504,953 S 5/2005 Ryan
D516,217 S 2/2006 Brown et al.
D522,657 S 6/2006 Murphy et al.
7,066,949 B2 6/2006 Gammons et al.
7,153,294 B1 12/2006 Farrow
D537,944 S 3/2007 Eda et al.
7,198,046 B1 4/2007 Argenta et al.
D544,092 S 6/2007 Lewis
7,240,676 B2 7/2007 Rutter
D548,347 S 8/2007 Ichino et al.
D551,578 S 9/2007 Kuriger et al.
7,367,342 B2 5/2008 Butler
7,438,705 B2 10/2008 Karpowicz et al.
D580,285 S 11/2008 Hendrickson et al.
D585,137 S 1/2009 Onoda et al.
7,524,315 B2 4/2009 Blott et al.
D593,676 S 6/2009 Locke et al.
D594,114 S 6/2009 Locke et al.
7,569,742 B2 8/2009 Haggstrom et al.
D602,583 S 10/2009 Pidgeon et al.
7,604,610 B2 10/2009 Shener et al.
7,608,066 B2 10/2009 Vogel
7,611,500 B1 11/2009 Lina et al.
7,615,036 B2 11/2009 Joshi et al.
7,625,362 B2 12/2009 Boehringer et al.
7,670,323 B2 3/2010 Hunt et al.
D617,094 S 6/2010 Pidgeon et al.
D617,461 S 6/2010 Kaushal et al.
7,731,702 B2 6/2010 Bybordi et al.
7,758,554 B2 7/2010 Lina et al.
7,794,450 B2 9/2010 Blott et al.
7,837,673 B2 11/2010 Vogel
7,857,806 B2 12/2010 Karpowicz et al.
D630,313 S 1/2011 Pidgeon et al.
D630,725 S 1/2011 Pidgeon et al.
7,927,318 B2 4/2011 Risk, Jr. et al.
7,976,598 B2 7/2011 Matula et al.
7,998,125 B2 8/2011 Weston
8,021,348 B2 9/2011 Risk, Jr. et al.
8,048,046 B2 11/2011 Hudspeth et al.
D650,894 S 12/2011 Gonzalez
8,157,792 B2 4/2012 Dolliver et al.
8,162,909 B2 4/2012 Blott et al.
8,172,817 B2 5/2012 Michaels et al.
8,235,972 B2 8/2012 Adahan
8,240,470 B2 8/2012 Pidgeon et al.
8,257,327 B2 9/2012 Blott et al.
8,267,909 B2 9/2012 Clementi et al.
8,294,586 B2 10/2012 Pidgeon et al.
8,303,555 B2 11/2012 Miau et al.
8,323,264 B2 12/2012 Weston et al.
8,333,744 B2 12/2012 Hartwell et al.
8,348,910 B2 1/2013 Blott et al.
D675,728 S 2/2013 Tout et al.
8,372,049 B2 2/2013 Jaeb et al.
D681,806 S 5/2013 Kataoka et al.
8,444,392 B2 5/2013 Turner et al.
8,494,349 B2 7/2013 Gordon
8,641,693 B2 2/2014 Locke et al.
8,814,840 B2 8/2014 Evans et al.
8,814,841 B2 8/2014 Hartwell
8,858,517 B2 10/2014 Pan et al.
8,974,429 B2 3/2015 Gordon et al.

(56) References Cited

U.S. PATENT DOCUMENTS

| | | | |
|---|---|---|---|
| 9,084,845 B2 | 7/2015 | Adie et al. | |
| 9,155,821 B2 | 10/2015 | Wudyka | |
| 9,211,486 B2 | 12/2015 | Locke et al. | |
| D750,222 S | 2/2016 | Chang | |
| 9,320,838 B2 | 4/2016 | Hartwell et al. | |
| 9,408,954 B2 | 8/2016 | Gordon et al. | |
| 9,561,312 B2 | 2/2017 | Heaton et al. | |
| 9,636,440 B2 | 5/2017 | Weston et al. | |
| D802,744 S | 11/2017 | Bjelovuk et al. | |
| D813,374 S | 3/2018 | Bjelovuk et al. | |
| D814,016 S | 3/2018 | Bjelovuk et al. | |
| D815,726 S | 4/2018 | Bjelovuk et al. | |
| 9,956,325 B2 | 5/2018 | Malhi | |
| 10,004,835 B2 | 6/2018 | Wiesner | |
| 10,328,188 B2 | 6/2019 | Deutsch et al. | |
| 10,898,621 B2 | 1/2021 | Chen et al. | |
| 11,013,639 B1 | 5/2021 | Temkin et al. | |
| 11,266,774 B2 | 3/2022 | Selby et al. | |
| 11,376,357 B2 | 7/2022 | Aarestad et al. | |
| 11,471,585 B2 | 10/2022 | Chang et al. | |
| 11,478,383 B2 | 10/2022 | Severns et al. | |
| 11,614,170 B2 | 3/2023 | Tumey et al. | |
| 2002/0145012 A1 | 10/2002 | Ho | |
| 2003/0101826 A1 | 6/2003 | Neubert | |
| 2003/0163101 A1 | 8/2003 | Say | |
| 2003/0181850 A1 | 9/2003 | Diamond et al. | |
| 2003/0212357 A1 | 11/2003 | Pace | |
| 2003/0235635 A1 | 12/2003 | Fong et al. | |
| 2004/0006319 A1* | 1/2004 | Lina | A61M 1/962 604/304 |
| 2004/0006321 A1 | 1/2004 | Cheng et al. | |
| 2004/0087918 A1 | 5/2004 | Johnson, III et al. | |
| 2004/0153029 A1 | 8/2004 | Blischak et al. | |
| 2004/0167482 A1 | 8/2004 | Watson | |
| 2004/0180093 A1 | 9/2004 | Burton et al. | |
| 2004/0233631 A1 | 11/2004 | Lord | |
| 2005/0144711 A1 | 7/2005 | Valadez et al. | |
| 2005/0166683 A1 | 8/2005 | Krivitski et al. | |
| 2005/0248045 A1 | 11/2005 | Anthony | |
| 2006/0059980 A1 | 3/2006 | Matsubara et al. | |
| 2006/0129137 A1 | 6/2006 | Lockwood et al. | |
| 2006/0280650 A1 | 12/2006 | Wong et al. | |
| 2007/0021697 A1 | 1/2007 | Ginther et al. | |
| 2007/0055209 A1 | 3/2007 | Patel et al. | |
| 2007/0118096 A1 | 5/2007 | Smith et al. | |
| 2007/0135779 A1 | 6/2007 | Lalomia et al. | |
| 2007/0219535 A1 | 9/2007 | Phung et al. | |
| 2008/0011667 A1 | 1/2008 | Ruschke | |
| 2008/0033400 A1 | 2/2008 | Holper et al. | |
| 2008/0125698 A1 | 5/2008 | Gerg et al. | |
| 2008/0183233 A1 | 7/2008 | Koch et al. | |
| 2008/0281281 A1 | 11/2008 | Meyer et al. | |
| 2009/0099519 A1 | 4/2009 | Kaplan | |
| 2009/0157016 A1 | 6/2009 | Adahan | |
| 2009/0204049 A1 | 8/2009 | Lee | |
| 2009/0240218 A1 | 9/2009 | Braga et al. | |
| 2009/0254066 A1 | 10/2009 | Heaton et al. | |
| 2009/0299251 A1 | 12/2009 | Buan | |
| 2009/0299306 A1 | 12/2009 | Buan | |
| 2009/0312725 A1 | 12/2009 | Braga | |
| 2010/0030132 A1 | 2/2010 | Niezgoda et al. | |
| 2010/0036333 A1 | 2/2010 | Schenk, III et al. | |
| 2010/0318043 A1 | 12/2010 | Malhi et al. | |
| 2010/0318071 A1 | 12/2010 | Wudyka | |
| 2011/0038741 A1 | 2/2011 | Lissner et al. | |
| 2011/0106027 A1 | 5/2011 | Vess et al. | |
| 2011/0112493 A1 | 5/2011 | Koch et al. | |
| 2011/0130712 A1 | 6/2011 | Topaz | |
| 2011/0313375 A1 | 12/2011 | Michaels | |
| 2012/0000478 A1 | 1/2012 | Wagenhals | |
| 2012/0035560 A1 | 2/2012 | Eddy et al. | |
| 2012/0123358 A1 | 5/2012 | Hall et al. | |
| 2013/0144227 A1 | 6/2013 | Locke et al. | |
| 2013/0144235 A1 | 6/2013 | Augustine et al. | |
| 2014/0207091 A1 | 7/2014 | Heagle et al. | |
| 2014/0276494 A1 | 9/2014 | Cisko et al. | |
| 2014/0320283 A1 | 10/2014 | Lawhorn | |
| 2016/0184498 A1 | 6/2016 | Jaeb et al. | |
| 2016/0287765 A1 | 10/2016 | Canner et al. | |
| 2017/0216501 A1 | 8/2017 | Armstrong et al. | |
| 2018/0104387 A1 | 4/2018 | Braga et al. | |
| 2018/0304065 A1 | 10/2018 | Armstrong et al. | |
| 2018/0333521 A1 | 11/2018 | Hudspeth et al. | |
| 2018/0353352 A1 | 12/2018 | Fink et al. | |
| 2019/0009008 A1 | 1/2019 | Hartwell | |
| 2019/0059807 A1* | 2/2019 | Su | A61B 5/4809 |
| 2019/0060532 A1 | 2/2019 | Hartwell et al. | |
| 2019/0099527 A1 | 4/2019 | Schuessler et al. | |
| 2020/0171217 A9 | 6/2020 | Braga et al. | |
| 2022/0001100 A1 | 1/2022 | Pratt et al. | |

FOREIGN PATENT DOCUMENTS

| | | |
|---|---|---|
| EP | 0358302 A2 | 3/1990 |
| EP | 2223711 A1 | 9/2010 |
| EP | 2248546 A2 | 11/2010 |
| GB | 1415096 A | 11/1975 |
| GB | 2418738 A | 4/2006 |
| JP | 2000202022 A | 7/2000 |
| WO | WO-8700439 A1 | 1/1987 |
| WO | WO-03022333 A1 | 3/2003 |
| WO | WO-03053346 A2 | 7/2003 |
| WO | WO-2007087808 A1 | 8/2007 |
| WO | WO-2007087809 A1 | 8/2007 |
| WO | WO-2009077722 A1 | 6/2009 |
| WO | WO-2009086580 A1 | 7/2009 |
| WO | WO-2011079144 A2 | 6/2011 |
| WO | WO-2019169327 A1 | 9/2019 |
| WO | WO-2020018328 A1 | 1/2020 |
| WO | WO-2020061334 A1 | 3/2020 |
| WO | WO-2020176331 A1 | 9/2020 |
| WO | WO-2020263508 A1 | 12/2020 |
| WO | WO-2021028773 A1 | 2/2021 |
| WO | WO-2021059209 A1 | 4/2021 |
| WO | WO-2023094915 A1 | 6/2023 |

OTHER PUBLICATIONS

International Search Report and Written Opinion for Application No. PCT/EP2022/060463, mailed on Oct. 24, 2022, 20 pages.

KCI, “V.A.C. Freedom User’s Guide,” May 2002, 16 pages.

Piaggesi A., et al., “SNAP® Wound Care System Made Easy,” Wounds International, retrieved from URL: http://www.woundsinternational.com, vol. 3 (1), Feb. 2012, 6 pages.

The Free Dictionary, “Evaporation,” The American Heritage®, Science Dictionary, 2005, 3 pages.

International Preliminary Report on Patentability for Application No. PCT/EP2022/060463, mailed on Nov. 2, 2023, 14 pages.

* cited by examiner

Tampered

Not tampered

CANISTER STATUS DETERMINATION FOR NEGATIVE PRESSURE WOUND THERAPY DEVICES

CROSS-REFERENCE TO RELATED APPLICATIONS

This application is a U.S. national stage application of International Patent Application No. PCT/EP2022/060463, filed Apr. 20, 2022, which claims priority to Patent Application No. EP 21382346.1, filed on Apr. 21, 2021, which are hereby incorporated by reference in its entirety and made part of this disclosure.

TECHNICAL FIELD

Embodiments described herein relate to apparatuses, systems, and methods for the treatment of wounds, for example using dressings in combination with negative pressure wound therapy.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

SUMMARY

A negative pressure wound therapy device can include a device housing, a negative pressure source supported by the device housing, the negative pressure source configured to provide negative pressure to a wound covered by a wound dressing, and a canister configured to be in fluid communication with the negative pressure source and the wound dressing, the canister can comprise a canister housing configured to store fluid aspirated from the wound, a cap connected to the canister housing and configured to be connected to the device housing when the canister is removably attached to the device housing, and a fluid level sensor supported by the cap, the fluid level sensor comprising a pair of arms extending into an interior of the canister housing and configured to be in fluid communication with fluid aspirated from the wound, wherein the fluid level sensor is configured to detect a completed electrical circuit when the fluid aspirated from the wound comes into contact with the pair of arms of the fluid level sensor, and wherein the fluid level sensor is configured to detect a canister full condition when the electrical circuit is completed, and an electronic circuitry configured to detect a state of the fluid level sensor and provide an indication of a status of the canister.

The negative pressure wound therapy device of any of the preceding paragraphs and/or any of the apparatuses, systems, or devices disclosed herein can include one or more of the following features. The status of the canister can comprise the canister full condition. The electronic circuitry can be supported by the device housing. The fluid level sensor can be configured to communicate with the electronic circuitry using Near Field Communication (NFC). The fluid level sensor can comprise a Near Field Communication (NFC) tamper detection circuitry, and wherein responsive to the fluid aspirated from the wound completing a circuit in the NFC tamper detection circuitry, the fluid level sensor is configured to detect the canister full condition. The electronic circuitry can comprise an antenna configured to communicate with the NFC tamper detection circuitry and facilitate transmission and reception of data.

A canister for negative pressure wound therapy can include a canister housing configured to store fluid removed from a wound and a fluid level sensor comprising a pair of arms extending into an interior of the canister housing and configured to be in fluid communication with fluid removed from the wound, wherein the fluid level sensor is configured to detect a completed electrical circuit when fluid within the interior of the canister comes in contact with the pair of arms of the fluid level sensor, and wherein the fluid level sensor is configured to detect a canister full condition when the electrical circuit is closed, wherein a reader is configured to wirelessly detect a state of the fluid level sensor and provide an indication of a status of the canister.

The negative pressure wound therapy device or canister for negative pressure wound therapy of any of the preceding paragraphs and/or any of the apparatuses, systems, or devices disclosed herein can include one or more of the following features. The status of the canister can comprise the canister full condition. The fluid level sensor can be configured to communicate with the reader using Near Field Communication (NFC). The fluid level sensor can comprise a Near Field Communication (NFC) tamper detection circuitry, wherein responsive to the fluid removed from the wound completing a circuit in the NFC tamper detection circuitry, the fluid level sensor is configured to detect the canister full condition. The reader can comprise an antenna configured to wirelessly communicate with the NFC tamper detection circuitry. The canister can further comprise a cap connected to the canister housing and configured to be connected to a negative pressure wound therapy device when the canister housing is removably attached to the negative pressure wound therapy device, wherein the fluid level sensor is supported by the cap.

A negative pressure wound therapy device can include a device housing, a negative pressure source supported by the device housing, the negative pressure source configured to provide negative pressure to a wound covered by a wound dressing, a device coil supported by the device housing, and a canister comprising a canister housing configured to collect fluid removed from the wound, a plurality of electrodes extending into the canister housing, and a canister coil connected to the plurality of electrodes and configured to be in electrical communication with fluid within the canister, wherein the canister coil is configured to conduct a current when the fluid in the canister comes into contact with the plurality of electrodes, and wherein the current in the canister coil causes a change of current in the device coil indicating a fluid level of fluid collected in the canister housing, and an electronic circuitry configured to detect the change of current and generate an indication of the fluid level.

The negative pressure wound therapy device of any of the preceding paragraphs and/or any of the apparatuses, systems, or devices disclosed herein can include one or more of the following features. The electronic circuitry can be supported by the device housing.

A canister fluid level detection system can include a device electronic circuitry comprising a device coil, and a canister comprising a canister housing configured to collect fluid removed from a wound, and a canister coil configured to be in electrical communication with fluid within the canister, wherein the canister coil is configured to conduct a current when the fluid in the canister reaches a fluid level threshold, and wherein the current in the canister coil causes a change in a current conducted by the device coil indicating a fluid level within the canister, wherein the device electronic circuitry is configured to detect the change in the current conducted by the device coil and generate an indication of the fluid level.

Disclosed herein are methods of operating a negative pressure wound therapy device of any of the preceding paragraphs and/or any of the devices, apparatuses, or systems disclosed herein.

Disclosed herein are kits that include the negative pressure wound therapy device of any of the preceding paragraphs and/or any of the devices, apparatuses, or systems disclosed herein and one or more wound dressings.

Any of the features, components, or details of any of the arrangements or embodiments disclosed in this application, including without limitation any of the apparatus embodiments and any of the negative pressure wound therapy embodiments disclosed herein, are interchangeably combinable with any other features, components, or details of any of the arrangements or embodiments disclosed herein to form new arrangements and embodiments.

DETAILED DESCRIPTION

Figure 1A:
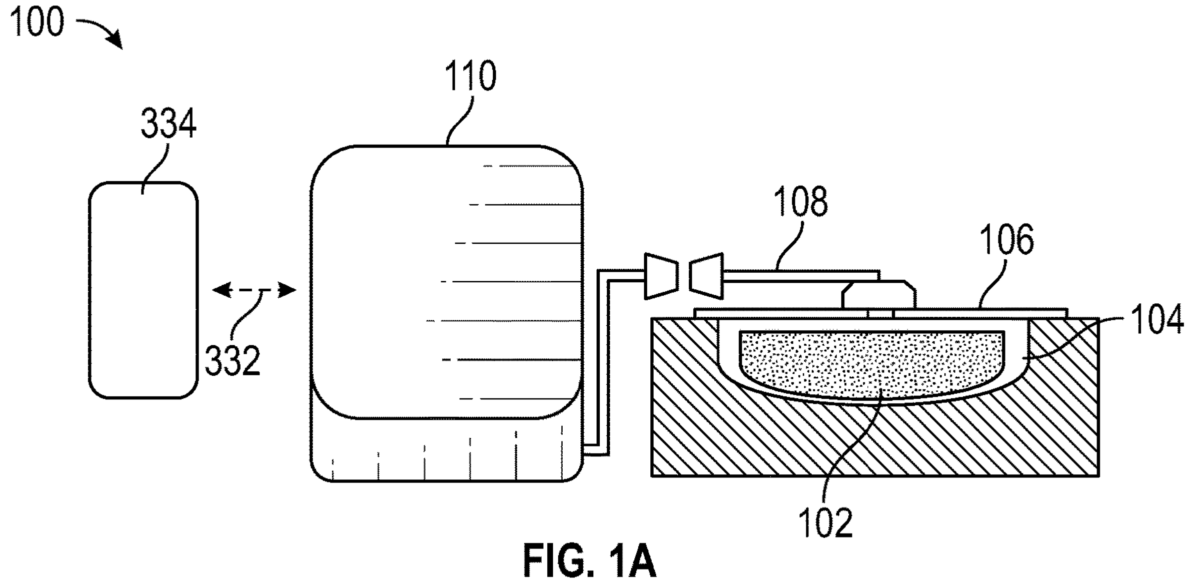
FIG. 1A illustrates a negative pressure wound therapy system.

Embodiments disclosed herein relate to systems and methods of treating and/or monitoring a wound. Some embodiments of the negative pressure wound therapy devices disclosed herein can include a negative pressure source configured to be connected and/or fluidically coupled, via a fluid flow path, to a wound covered by a wound dressing and provide negative pressure to a wound.

Throughout this specification reference is made to a wound. The term wound is to be broadly construed and encompasses open and closed wounds in which skin is torn, cut or punctured or where trauma causes a contusion, or any other superficial or other conditions or imperfections on the skin of a patient or otherwise that benefit from pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

As used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects pressure that is X mmHg below 760 mmHg or, in other words, a pressure of (760−X) mmHg. In addition, negative pressure that is "less" or "smaller" than X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A healthcare provider, such as a clinician, nurse, or the like, can provide a TNP prescription specifying, for example, the pressure level or time of application. However, the healing process is different for each patient and the prescription may affect the healing process in a way the clinician or healthcare provider did not expect at the time of devising the prescription. A healthcare provider may try to adjust the prescription as the wound heals (or does not heal), but such process may require various appointments that can be time consuming and repetitive. Embodiments disclosed herein provide systems, devices, or methods of efficiently adjusting TNP prescriptions and delivering effective TNP therapy.

Wound Therapy System

FIG. 1A schematically illustrates a negative pressure wound treatment system 100 (sometimes referred to as a reduced or negative pressure wound therapy system, a TNP system, or a wound treatment system). In any implementations disclosed herein, though not required, the negative pressure wound treatment system 100 can include a wound filler 102 placed on or inside a wound 104 (which may be a cavity). The wound 104 can be sealed by a wound cover 106, which can be a drape, such that the wound cover 106 can be in fluidic communication with the wound 104. The wound filler 102 in combination with the wound cover 106 can be referred to as a wound dressing. A tube or conduit 108 (also referred to herein as a flexible suction adapter or a fluidic connector) can be used to connect the wound cover 106 with a wound therapy device 110 (sometimes as a whole or partially referred to as a "pump assembly") configured to supply reduced or negative pressure. The conduit 108 can be a single or multi lumen tube. A connector can be used to removably and selectively couple a conduit or tube 142 with the conduit 108.

In any of the systems disclosed herein, a wound therapy device can be canisterless, wherein, for example and without limitation, wound exudate is collected in the wound dressing or is transferred via a conduit for collection at another location. However, any of the wound therapy devices disclosed herein can include or support a canister.

Additionally, with any of the wound therapy systems disclosed herein, any of the wound therapy devices can be mounted to or supported by the wound dressing or adjacent to the wound dressing. The wound filler 102 can be any suitable type, such as hydrophilic or hydrophobic foam, gauze, inflatable bag, and so on. The wound filler 102 can be conformable to the wound 104 such that the wound filler 102 substantially fills the cavity of the wound 104. The wound cover 106 can provide a substantially fluid impermeable seal over the wound 104. The wound cover 106 can have a top side and a bottom side. The bottom side can adhesively (or in any other suitable manner) seal with the wound 104, for example by sealing with the skin around the wound 104. The conduit 108 or any other conduit disclosed herein can be formed from polyurethane, PVC, nylon, polyethylene, silicone, or any other suitable material.

The wound cover 106 can have a port (not shown) configured to receive an end of the conduit 108. In some cases, the conduit 108 can otherwise pass through or under the wound cover 106 to supply reduced pressure to the wound 104 so as to maintain a desired level of reduced pressure in the wound 104. The conduit 108 can be any suitable article configured to provide at least a substantially sealed fluid flow pathway or path between the wound therapy device 110 and the wound cover 106, so as to supply the reduced pressure provided by the wound therapy device 110 to wound 104.

The wound cover 106 and the wound filler 102 can be provided as a single article or an integrated single unit. In some cases, no wound filler is provided and the wound cover by itself may be considered the wound dressing. The wound dressing can then be connected, via the conduit 108, to a source of negative pressure of the wound therapy device 110. In some cases, though not required, the wound therapy device 110 can be miniaturized and portable, although larger conventional negative pressure sources (or pumps) can also be used.

The wound cover 106 can be located over a wound site to be treated. The wound cover 106 can form a substantially sealed cavity or enclosure over the wound. The wound cover 106 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate.

The wound therapy device 110 can operate with or without the use of an exudate canister. In some cases, as is illustrated, the wound therapy device 110 can include an exudate canister. In some cases, configuring the wound therapy device 110 and conduit 108 so that the conduit 108 can be quickly and easily removed from the wound therapy device 110 can facilitate or improve the process of wound dressing or pump changes, if necessary. Any of the pump assemblies disclosed herein can have any suitable connection between the conduit 108 and the pump.

The wound therapy device 110 can deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the wound therapy device 110.

As will be described in greater detail below, the negative pressure wound treatment system 100 can be configured to provide a connection 332 to a separate or remote computing device 334. The connection 332 can be wired or wireless (such as, Bluetooth, Bluetooth low energy (BLE), Near-Field Communication (NFC), WiFi, or cellular). The remote computing device 334 can be a smartphone, a tablet, a laptop or another standalone computer, a server (such as, a cloud server), another pump device, or the like.

Figure 1B:
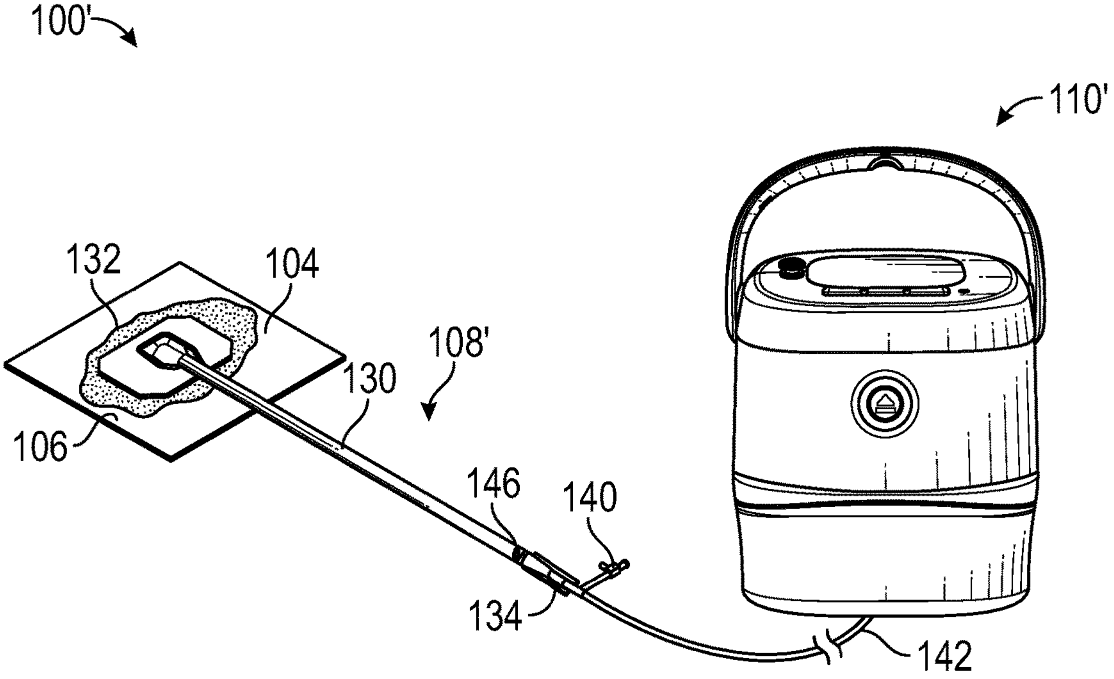
FIG. 1B illustrates another negative pressure wound therapy system.

FIG. 1B illustrates another negative pressure wound treatment system 100'. The negative pressure wound treatment system 100' can have any of the components, features, or other details of any of the other negative pressure wound treatment system disclosed herein, including without limitation the negative pressure wound treatment system 100 illustrated in FIG. 1A or the negative pressure wound treatment system 400 illustrated in FIG. 4, in combination with or in place of any of the components, features, or other details of the negative pressure wound treatment system 100' shown in FIG. 1B and/or described herein. The negative pressure wound treatment system 100' can have a wound cover 106 over a wound 104 that can seal the wound 104. A conduit 108', such as a single or multi lumen tube can be used to connect the wound cover 106 with a wound therapy device 110' (sometimes as a whole or partially referred to as a "pump assembly") configured to supply reduced or negative pressure. The wound cover 106 can be in fluidic communication with the wound 104.

With reference to FIG. 1B, the conduit 108' can have a bridge portion 130 that can have a proximal end portion and a distal end portion (the distal end portion being closer to the wound 104 than the proximal end portion, and an applicator 132 at the distal end of the bridge portion 130 forming the flexible suction adapter (or conduit) 108'. A connector 134 can be disposed at the proximal end of the bridge portion 130, so as to connect to at least one of the channels that can extend along a length of the bridge portion 130 of the conduit 108 shown in FIG. 1B. A cap 140 can be coupled with a portion of the conduit 108 and can, in some cases, as illustrated, be attached to the connector 134. The cap 140 can be useful in preventing fluids from leaking out of the proximal end of the bridge portion 130. The conduit 108' can be a Soft Port manufactured by Smith & Nephew. As mentioned, the negative pressure wound treatment system 100' can include a source of negative pressure, such as the device 110', capable of supplying negative pressure to the wound 104 through the conduit 108'. Though not required, the device 110' can also include a canister or other container for the storage of wound exudates and other fluids that can be removed from the wound.

The device 110' can be connected to the connector 134 via a conduit or tube 142. In use, the applicator 132 can be placed over an aperture formed in a cover 106 that is placed over a suitably-prepared wound or wound 104. Subsequently, with the wound therapy device 110' connected via the tube 142 to the connector 134, the wound therapy device 110' can be activated to supply negative pressure to the wound. Application of negative pressure can be applied until a desired level of healing of the wound is achieved.

The bridge portion 130 can comprise an upper channel material or layer positioned between an upper layer and an intermediate layer, with a lower channel material or layer positioned between the intermediate layer and a bottom layer. The upper, intermediate, and lower layers can have elongate portions extending between proximal and distal ends and can include a material that is fluid-impermeable, for example polymers such as polyurethane. It will of course be appreciated that the upper, intermediate, and lower layers can each be constructed from different materials, including semi-permeable materials. In some cases, one or more of the upper, intermediate, and lower layers can be at least partially transparent. In some instances, the upper and lower layers can be curved, rounded or outwardly convex over a majority of their lengths.

The upper and lower channel layers can be elongate layers extending from the proximal end to the distal end of the bridge 130 and can each preferably comprise a porous material, including for example open-celled foams such as polyethylene or polyurethane. In some cases, one or more of the upper and lower channel layers can be comprised of a fabric, for example a knitted or woven spacer fabric (such as a knitted polyester 3D fabric, Baltex 7970®, or Gehring 879®) or a nonwoven material, or terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure or vented air to the wound site, and can also confer a degree of kinking or occlusion resistance to the channel layers. In one example, the upper channel layer can include an open-celled foam such as polyurethane, and the lower channel layer can include a fabric. In another example, the upper channel layer is optional, and the system can instead be provided with an open upper channel. The upper channel layer can have a curved, rounded or upwardly convex upper surface and a substantially flat lower surface, and the lower channel layer can have a curved, rounded or downwardly convex lower surface and a substantially flat upper surface.

The fabric or material of any components of the bridge 130 can have a three-dimensional (3D) structure, where one or more types of fibers form a structure where the fibers extend in all three dimensions. Such a fabric can in some cases aid in wicking, transporting fluid or transmitting negative pressure. In some cases, the fabric or materials of the channels can include several layers of material stacked or layered over each other, which can in some cases be useful in preventing the channel from collapsing under the application of negative pressure. The materials used in some implementations of the conduit 108' can be conformable and pliable, which can, in some cases, help to avoid pressure ulcers and other complications which can result from a wound treatment system being pressed against the skin of a patient.

The distal ends of the upper, intermediate, and lower layers and the channel layers can be enlarged at their distal ends (to be placed over a wound site), and can form a "teardrop" or other enlarged shape. The distal ends of at least the upper, intermediate, and lower layers and the channel layers can also be provided with at least one through aperture. This aperture can be useful not only for the drainage of wound exudate and for applying negative pressure to the wound, but also during manufacturing of the device, as these apertures can be used to align these respective layers appropriately.

In some implementations, a controlled gas leak 146 (sometimes referred to as gas leak, air leak, or controlled air leak) can be disposed on the bridge portion 130, for example at the proximal end thereof. This air leak 146 can comprise an opening or channel extending through the upper layer of the bridge portion 130, such that the air leak 146 is in fluidic communication with the upper channel of the bridge portion 130. Upon the application of suction to the conduit 108, gas (such, as air) can enter through the gas leak 146 and move from the proximal end of the bridge portion 130 to the distal end of the bridge portion along the upper channel of the bridge portion 130. The gas can then be suctioned into the lower channel of the bridge portion 130 by passing through the apertures through the distal ends of the upper, intermediate, and lower layers.

The air leak 146 can include a filter. Preferably, the air leak 146 is located at the proximal end of the bridge portion 130 so as to minimize the likelihood of wound exudate or other fluids coming into contact and possibly occluding or interfering with the air leak 146 or the filter. In some instances, the filter can be a microporous membrane capable of excluding microorganisms and bacteria, and which may be able to filter out particles larger than 45 μm. Preferably, the filter can exclude particles larger than 1.0 μm, and more preferably, particles larger than 0.2 μm. Advantageously, some implementations can provide for a filter that is at least partially chemically-resistant, for example to water, common household liquids such as shampoos, and other surfactants. In some cases, reapplication of vacuum to the suction adapter or wiping of the exposed outer portion of the filter may be sufficient to clear any foreign substance occluding the filter. The filter can be composed of a suitably-resistant polymer such as acrylic, polyethersulfone, or polytetrafluoroethylene, and can be oleophobic or hydrophobic. In some cases, the gas leak 146 can supply a relatively constant gas flow that does not appreciably increase as additional negative pressure is applied to the conduit 108'. In instances of the negative pressure wound treatment system 100 where the gas flow through the gas leak 146 increases as additional negative pressure is applied, preferably this increased gas flow will be minimized and not increase in proportion to the negative pressure applied thereto. Further description of such bridges, conduits, air leaks, and other components, features, and details that can be used with any implementations of the negative pressure wound treatment systems disclosed herein are found in U.S. Pat. No. 8,801,685, which is incorporated by reference in its entirety as if fully set forth herein.

Any of the wound therapy devices (such as, the device 110 or 110') disclosed herein can provide continuous or intermittent negative pressure therapy. Continuous therapy can be delivered at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. Intermittent therapy can be delivered between low and high negative pressure set points (sometimes referred to as setpoint). Low set point can be set at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values.

In operation, the wound filler 102 can be inserted into the cavity of the wound 104, and wound cover 106 can be placed so as to seal the wound 104. The wound therapy device 110' can provide negative pressure to the wound cover 106, which can be transmitted to the wound 104 via the wound filler 102. Fluid (such as, wound exudate) can be drawn through the conduit 108' and stored in a canister. In some cases, fluid is absorbed by the wound filler 102 or one or more absorbent layers (not shown).

Wound dressings that can be utilized with the pump assembly and systems of the present application include Renasys-F, Renasys-G, Renasys AB, and Pico Dressings available from Smith & Nephew. Further description of such wound dressings and other components of a negative pressure wound therapy system that can be used with the pump assembly and systems of the present application are found in U.S. Patent Publication Nos. 2012/0116334, 2011/0213287, 2011/0282309, 2012/0136325, U.S. Pat. No. 9,084,845, and International App. No. PCT/EP2020/078376, each of which is incorporated by reference in its entirety as if fully set forth herein. In some cases, other suitable wound dressings can be utilized.

Figure 2A:
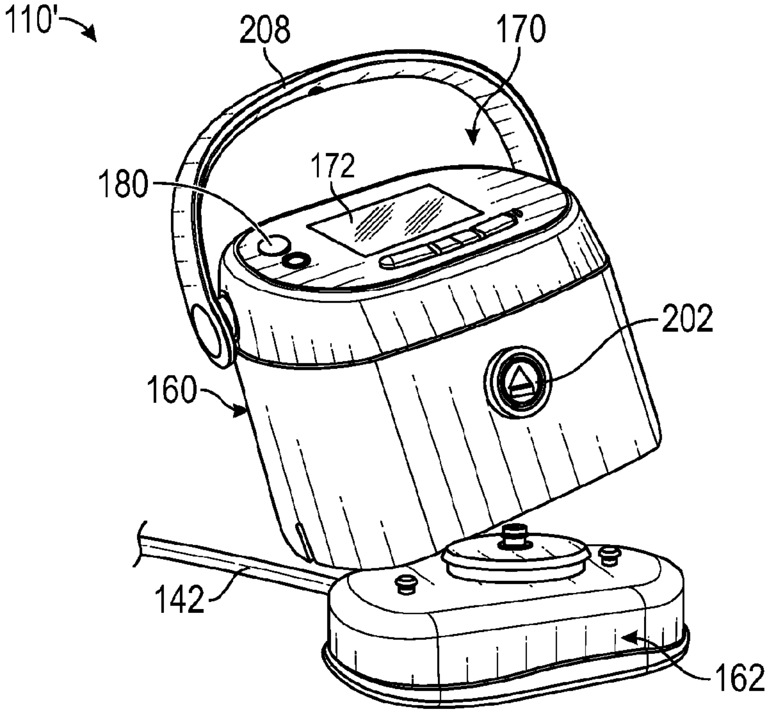
FIG. 2A is an isometric view of a negative pressure wound therapy device and canister, showing the canister detached from the pump assembly of the device.
Figure 2B:
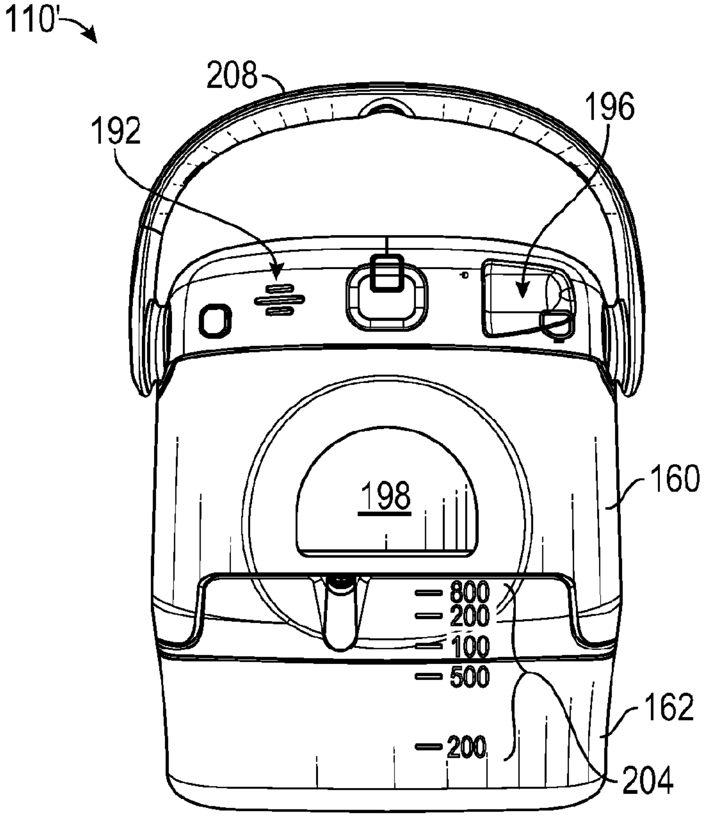
FIG. 2B is a back view of the negative pressure wound therapy device shown in FIG. 2A.
Figure 2C:
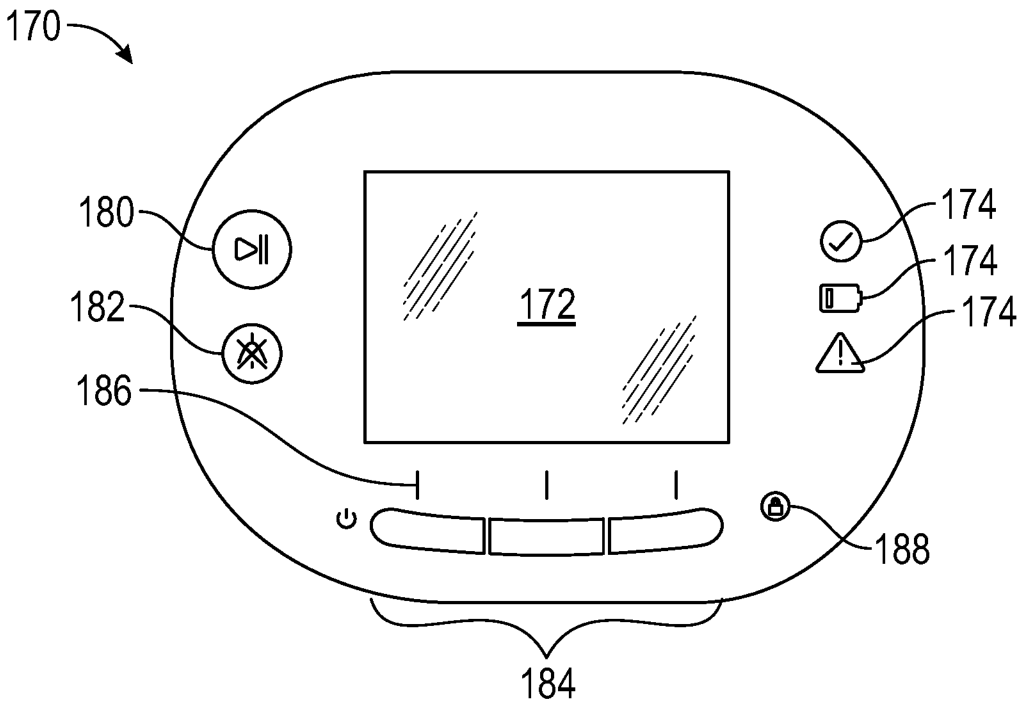
FIG. 2C illustrates a top surface of the negative pressure wound therapy device shown in FIG. 2A, showing a graphical user interface.

FIGS. 2A-2C show the negative pressure wound therapy device 110'. As illustrated, a pump assembly 160 and canister 162 can be connected, thereby forming the wound therapy device 110'. With reference to FIG. 2C, the pump assembly 160 can include an interface panel 170 having a display 172, one or more indicators 174, or one or more controls or buttons, including, for example and without limitation, a therapy start and pause button 180 or an alarm/alert mute button 182. The interface panel 170 can have one or more input controls or buttons 184 (three being shown) that can be used to control any functions of the pump assembly 160 or the interface panel 170. For example and without limitation, one or more of the buttons 184 can be used to turn the pump assembly 160 on or off, to start or pause therapy, to operate and monitor the operation of the pump assembly 160, to scroll through menus displayed on the display 172, or to control or perform other functions. In some cases, the command buttons 184 can be programmable, and can be made from a tactile, soft rubber.

Additionally, the interface panel 170 can have visual indicators 186 that can indicate which of the one or more buttons 184 is active. The interface panel 170 can also have a lock/unlock control or button 188 that can be configured to selectively lock or unlock the functionality of the various buttons (e.g., buttons 184) or the display 172. For example, therapy setting adjustment can be locked/unlocked via the lock/unlock control 188. When the lock/unlock button 188 is in the locked state, depressing one or more of the various other buttons or the display will not cause the pump assembly 160 to change any display functions or performance functions of the device. In some cases, when the lock/unlock button 188 is in the locked state, some buttons or portions of the display may be available and able to cause the pump assembly 160 to change any display functions or performance functions of the device while other buttons or portion of the display are not able to cause the pump assembly 160 to change any display functions or performance functions of the device. For example and without limitation, when the lock/unlock button 188 is in the locked state, the menu navigation may still be available and able to be used or activated, but the commands that adjust therapy settings are greyed out, and not able to be used or not able to cause a change of function of the device. This way, the interface panel 170 will be protected from inadvertent bumping or touching of the various buttons or display. The interface panel 170 can be located on an upper portion of the pump assembly 160, for example and without limitation on an upward facing surface of the pump assembly 160.

The display 172, which can be a screen such as an LCD screen, can be mounted in a middle portion of the interface panel 170. The display 172 can be a touch screen display. The display 172 can support playback of audiovisual (AV) content, such as instructional videos, and render a number of screens or graphical user interfaces (GUIs) for configuring, controlling, and monitoring the operation of the pump assembly 160.

The one or more indicators 174 can be lights (such as, LEDs) and can be configured to provide a visual indication of alarm conditions and/or a status of the pump. For example and without limitation, the one or more indicators 174 can be configured to provide a visual indication of a status of the pump assembly 160 or other components of the negative pressure wound treatment system 100', including without limitation the conduit 108' or the wound cover 106 (such as, to provide an indication of normal operation, low battery, a leak, canister full, blockage, overpressure, or the like). Any one or more suitable indicators can be additionally or alternatively used, such as visual, audio, tactile indicator, and so on.

FIG. 2B shows a back or rear view of the wound therapy device 110' shown in the FIG. 2A. As shown, the pump assembly 160 can include a speaker 192 for producing sound. For example and without limitation, the speaker 192 can generate an acoustic alarm in response to deviations in therapy delivery, non-compliance with therapy delivery, or any other similar or suitable conditions or combinations thereof. The speaker 192 can provide audio to accompany one or more instructional videos that can be displayed on the display 172.

The pump assembly 160 can be configured to provide easy access (such as, an access door on the casing of the pump assembly) to one or more filters of the pump assembly 160, such as antibacterial filters. This can enable a user (such as, a healthcare provider or patient) to more easily access, inspect or replace such filters. The pump assembly 160 can also include a power jack 196 for providing power to the pump assembly 160 or for charging and recharging an internal power source (such as, a battery). Some implementations of the pump assembly 160 can include a disposable or renewable power source, such as one or more batteries, so that no power jack is needed. The pump assembly 160 can have a recess 198 formed therein to facilitate gripping of the pump assembly 160.

The canister 162 can hold fluid aspirated from the wound 104. For example, the canister 162 can have an 800 mL (or approximately 800 mL) capacity, or from a 300 mL or less capacity to a 1000 mL or more capacity, or any capacity level in this range. The canister 162 can include a tubing for connecting to the conduit 108' in order to form a fluid flow path. The canister 162 can be replaced with another canister, such as when the canister 162 has been filled with fluid. With reference to FIG. 2A, the wound therapy device 110' can include a canister inlet tube 200 (also referred to herein as a dressing port connector) in fluid communication with the canister 162. For example and without limitation, the canister inlet tube 200 can be used to connect with the conduit 108'.

The canister 162 can be selectively coupleable and removable from the pump assembly 160. With reference to FIG. 2A, in some cases, a canister release button 202 can be configured to selectively release the canister 162 from the pump assembly 160. With reference to FIG. 2B, the canister 162 can have one or more fill lines or graduations 204 to indicate to the user and amount of fluid or exudate stored within the canister 162.

The wound therapy device 110' can have a handle 208 that can be used to lift or carry the wound therapy device 110'. The handle 208 can be coupled with the pump assembly 160 and can be rotatable relative to the wound therapy device 110' so that the handle can be rotated upward for lifting or carrying the wound therapy device 110' or the pump assembly 160, or rotated into a lower profile in a more compact position when the handle is not being used. In some cases, the handle 208 can be coupled with the pump assembly 160 in a fixed position. The handle 208 can be coupled with an upper portion of the pump assembly 160 or can be removable from the wound therapy device 110'.

Figure 3:
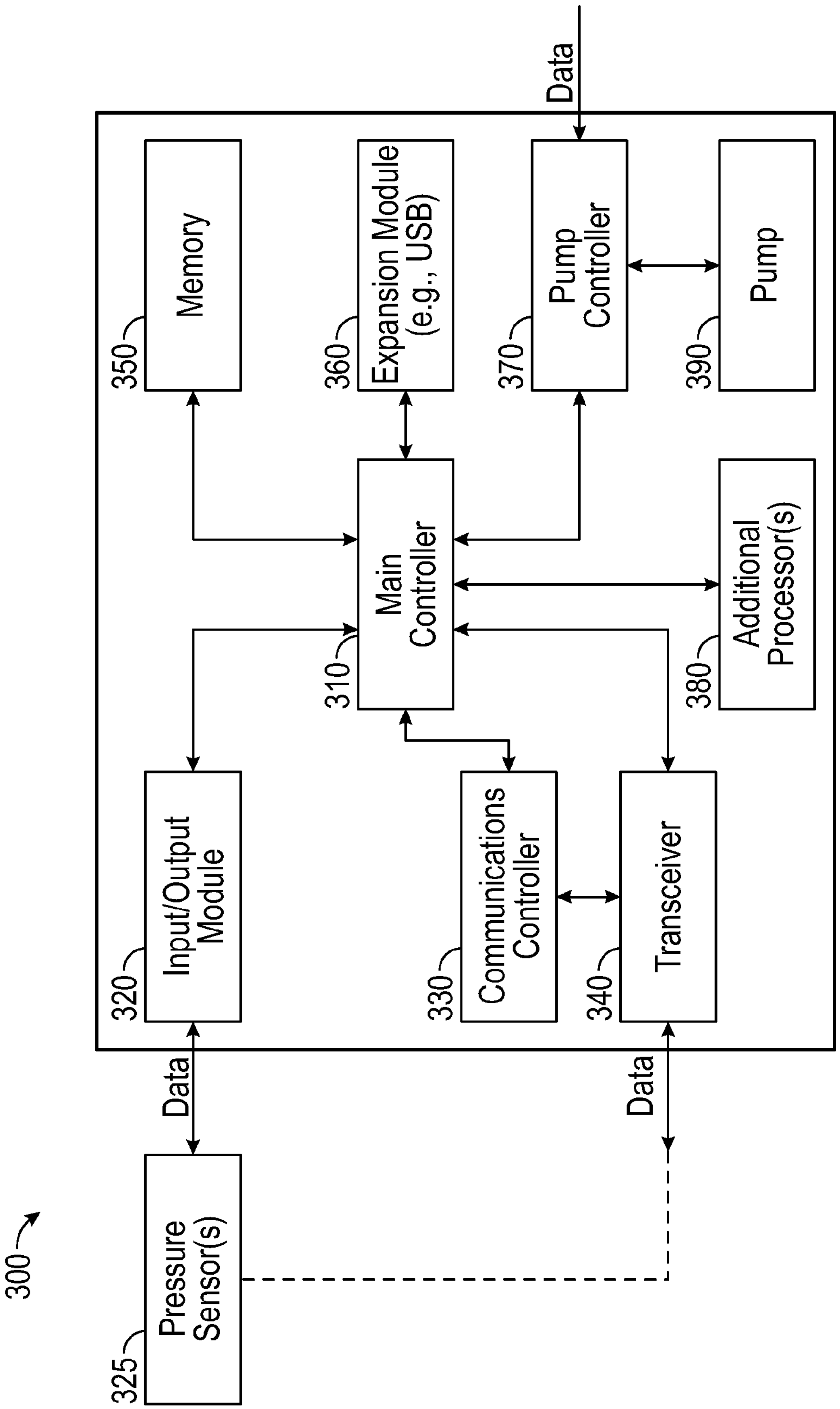
FIG. 3 illustrates a schematic of a control system of a negative pressure wound therapy device.

FIG. 3 illustrates a schematic of a control system 300 that can be employed in any of the wound therapy devices described herein, such as in the wound therapy device 110'. Electrical components can operate to accept user input, provide output to the user, operate the pressure source, provide connectivity, and so on. A first processor (such as, a main controller 310) can be responsible for user activity, and a second processor (such as, a pump controller 370) can be responsible for controlling another device, such as a pump 390.

An input/output (I/O) module 320 can be used to control an input and/or output to another component or device, such as the pump 390, one or more sensors (for example, one or more pressure sensors 325 configured to monitor pressure in one or more locations of the fluid flow path), or the like. For example, the I/O module can receive data from one or more sensors through one or more ports, such as serial (for example, I2C), parallel, hybrid ports, and the like. Any of the pressure sensors can be part of the wound therapy device or the canister. In some cases, any of the pressure sensors 325 can be remote to the wound therapy device, such as positioned at or near the wound (for example, in the dressing or the conduit connecting the dressing to the wound therapy device). In such implementations, any of the remote pressure sensors can communicate with the I/O module over a wired connection or with one or more transceivers 340 over a wireless connection.

The main controller 310 can receive data from and provide data to one or more expansion modules 360, such as one or more USB ports, SD ports, Compact Disc (CD) drives, DVD drives, FireWire ports, Thunderbolt ports, PCI Express ports, and the like. The main controller 310, along with other controllers or processors, can store data in memory 350 (such as one or more memory modules), which can be internal or external to the main controller 310. Any suitable type of memory can be used, including volatile or non-volatile memory, such as RAM, ROM, magnetic memory, solid-state memory, Magnetoresistive random-access memory (MRAM), and the like.

The main controller 310 can be a general purpose controller, such as a low-power processor or an application specific processor. The main controller 310 can be configured as a "central" processor in the electronic architecture of the control system 300, and the main controller 310 can coordinate the activity of other processors, such as the pump controller 370, one or more communications controllers 330, and one or more additional processors 380. The main controller 310 can run a suitable operating system, such as a Linux, Windows CE, VxWorks, etc.

The pump controller 370 can control the operation of a pump 390, which can generate negative or reduced pressure. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump controller 370 can measure pressure in a fluid flow path, using data received from one or more pressure sensors 325, calculate the rate of fluid flow, and control the pump. The pump controller 370 can control the pump actuator (such as, a motor) so that a desired level of negative pressure is achieved in the wound 104. The desired level of negative pressure can be pressure set or selected by the user. The pump controller 370 can control the pump (for example, pump motor) using pulse-width modulation (PWM) or pulsed control. A control signal for driving the pump can be a 0-100% duty cycle PWM signal. The pump controller 370 can perform flow rate calculations and detect alarms. The pump controller 370 can communicate information to the main controller 310. The pump controller 370 can be a low-power processor.

Any of the one or more communications controllers 330 can provide connectivity (such as, a wired or wireless connection 332). The one or more communications controllers 330 can utilize one or more transceivers 340 for sending and receiving data. The one or more transceivers 340 can include one or more antennas, optical sensors, optical transmitters, vibration motors or transducers, vibration sensors, acoustic sensors, ultrasound sensors, or the like. Any of the one or more transceivers 340 can function as a communications controller. In such case, the one or more communications controllers 330 can be omitted. Any of the one or more transceivers 340 can be connected to one or more antennas that facilitate wireless communication. The one or more communications controllers 330 can provide one or more of the following types of connections: Global Positioning System (GPS), cellular connectivity (for example, 2G, 3G, LTE, 4G, 5G, or the like), NFC, Bluetooth connectivity (or BLE), radio frequency identification (RFID), wireless local area network (WLAN), wireless personal area network (WPAN), WiFi connectivity, Internet connectivity, optical connectivity (for example, using infrared light, barcodes, such as QR codes, etc.), acoustic connectivity, ultrasound connectivity, or the like. Connectivity can be used for various activities, such as pump assembly location tracking, asset tracking, compliance monitoring, remote selection, uploading of logs, alarms, and other operational data, and adjustment of therapy settings, upgrading of software or firmware, pairing, and the like.

Any of the one or more communications controllers 330 can provide dual GPS/cellular functionality. Cellular functionality can, for example, be 3G, 4G, or 5G functionality. The one or more communications controllers 330 can communicate information to the main controller 310. Any of the one or more communications controllers 330 can include internal memory or can utilize memory 350. Any of the one or more communications controllers 330 can be a low-power processor.

The control system 300 can store data, such as GPS data, therapy data, device data, and event data. This data can be stored, for example, in memory 350. This data can include patient data collected by one or more sensors. The control system 300 can track and log therapy and other operational data. Such data can be stored, for example, in the memory 350.

Using the connectivity provided by the one or more communications controller 330, the control system 300 can upload any of the data stored, maintained, or tracked by the control system 300 to a remote computing device, such as the device 334. The control system 300 can also download various operational data, such as therapy selection and parameters, firmware and software patches and upgrades, and the like (for example, via the connection to the device 334). The one or more additional processors 380, such as processor for controlling one or more user interfaces (such as, one or more displays), can be utilized. In some cases, any of the illustrated or described components of the control system 300 can be omitted depending on an embodiment of a wound monitoring or treatment system in which the control system 300 is used.

Any of the negative pressure wound therapy devices described herein can include one or more features disclosed in U.S. Pat. No. 9,737,649 or U.S. Patent Publication No. 2017/0216501, each of which is incorporated by reference in its entirety.

Multiple Dressing Negative Wound Therapy

Figure 4:
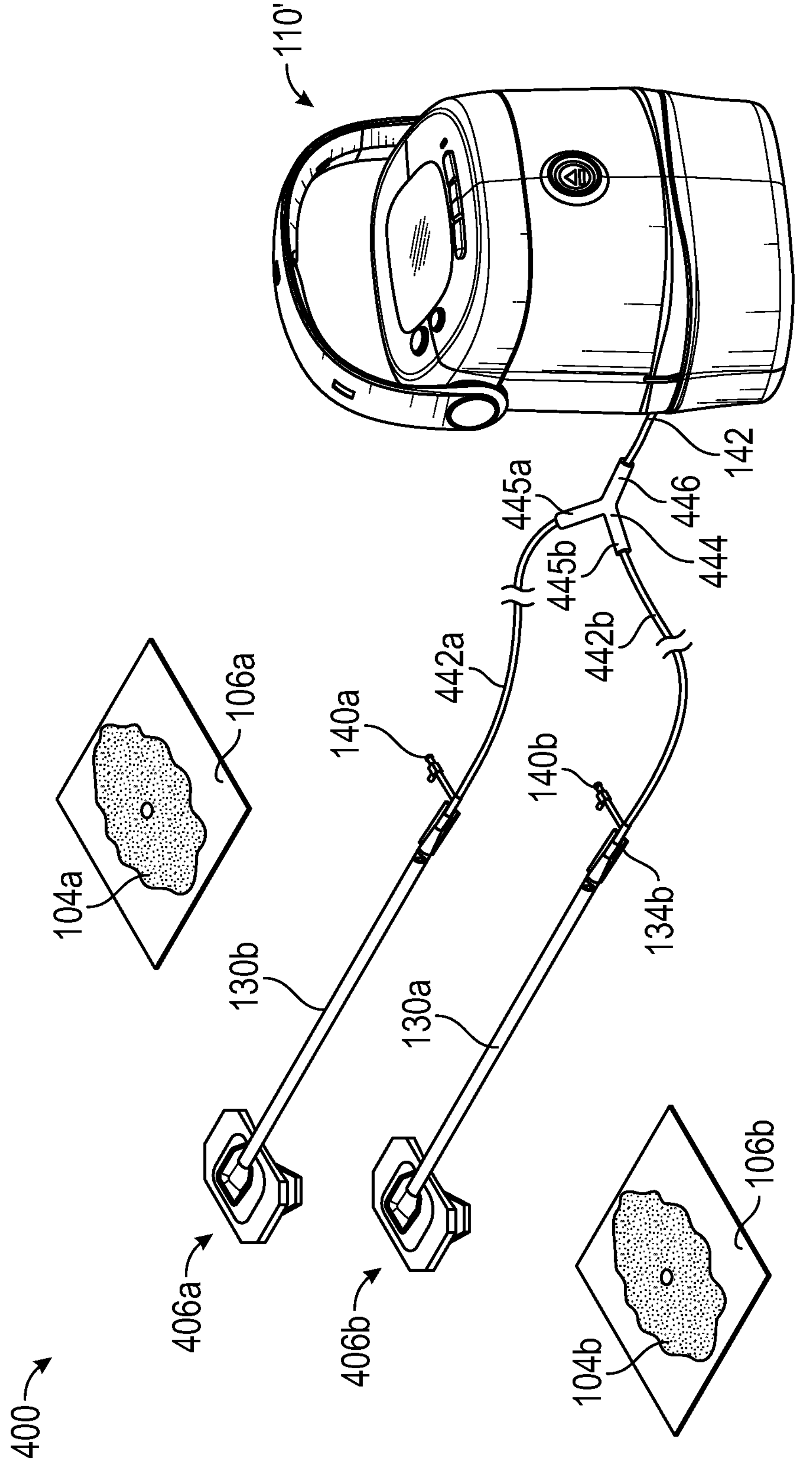
FIG. 4 illustrates another negative pressure wound therapy system.

FIG. 4 illustrates another negative pressure wound treatment system 400. The system 400 can include a wound therapy device capable of supplying negative pressure to the wound site or sites, such as wound therapy device 110'. The wound therapy device 110' can be in fluidic communication with one or more wound dressings 406*a*, 406*b* (collectively referred to as 406) so as to supply negative pressure to one or more wounds, such as the wounds 104*a* and 104*b*. A first fluid flow path can include components providing fluidic connection from the wound therapy device 110' to the first wound dressing 406*a*. As a non-limiting example, the first fluid flow path can include the path from the wound dressing 406*a* to the wound therapy device 110' or the path from the first wound dressing 406*a* to an inlet 446 of a branching attachment (or connector) 444 in fluidic connection with the wound therapy device 110'. Similarly, a second fluid flow path can include components providing fluidic connection from the wound therapy device 110' to the second wound dressing 406*b*.

The system 400 can be similar to the system 100' with the exception that multiple wounds 104*a* and 104*b* are being treated by the system 400. The system 400 can include any one or more of the components of the system 100', which are illustrated in FIG. 4 with appended letter "a" or "b" to distinguish between the first and second wounds (such as, the wounds 104*a* and 104*b*, the covers 106*a* and 106*b*). As illustrated, the system 400 can include a plurality of wound dressings 406*a*, 406*b* (and corresponding fluid flow paths) in fluidic communication with the wound therapy device 110' via a plurality of suction adapters, such as the adapter 108'. The suction adapters can include any one or more of the components of the adapter 108', which are illustrated in FIG. 4 with appended letter "a" or "b" to distinguish between the first and second wounds (such as, the bridge portions 130*a* and 130*b*, the connectors 134*a* and 134*b*, and the caps 140*a* and 140*b*).

The wound therapy device 110' can be fluidically coupled via the tube 142 with the inlet 446 of the connector 444. The connector 444 can be fluidically coupled via branches 445*a*, 445*b* and tubes or conduits 442*a*, 442*b* with the connectors 134*a*, 134*b*, which can be fluidically coupled with the tubes or conduits 130*a*, 130*b*. The tubes or conduits 130*a*, 130*b* can be fluidically coupled with the dressings 406*a*, 406*b*. Once all conduits and dressing components are coupled and operably positioned, the wound therapy device 110' can be activated, thereby supplying negative pressure via the fluid flow paths to the wounds 430*a*, 430*b*. Application of negative pressure can be applied until a desired level of healing of the wounds 430 is achieved. Although two wounds and wound dressing are illustrated in FIG. 4, some implementations of the wound therapy device 110' can provide treatment to a single wound (for instance, by closing the unused branch 445*a* or 445*b* of the connector 444) or to more than two wounds (for instance, by adding branches to the connector 444).

The system 400 can include one or more features disclosed in U.S. Patent Publication No. 2020/0069850 or International Publication No. WO2018/167199, each of which is incorporated by reference in its entirety.

Canister Status Detection

A negative pressure therapy system can utilize a canister status detection system. The canister status detection system can function as a fluid detection system to detect the volume of fluid (or liquid) within the canister (or fill level of the canister) or whether the canister has reached a full or almost full level of fluid (or liquid). One or more alarms or alerts can be generated responsive to the detection. A canister full or nearly full alert can be important for a negative pressure therapy system because it can allow a healthcare professional or a user to replace their canister and continue therapy with the least amount of interruptions (such as, not having to worry about the device suddenly sounding a canister full or canister blockage alarm).

Canister fluid detection systems may rely on comparing peak-to-peak voltage measurements obtained from a pressure sensor to threshold values over a certain period to then trigger the canister full or nearly full alert. In some cases, this approach can be unreliable and can have a low tolerance for variations in conditions. For instance, nuisance alarms may be generated when the canister is empty but there are restrictions in flow from the filter assembly.

Figure 5A:
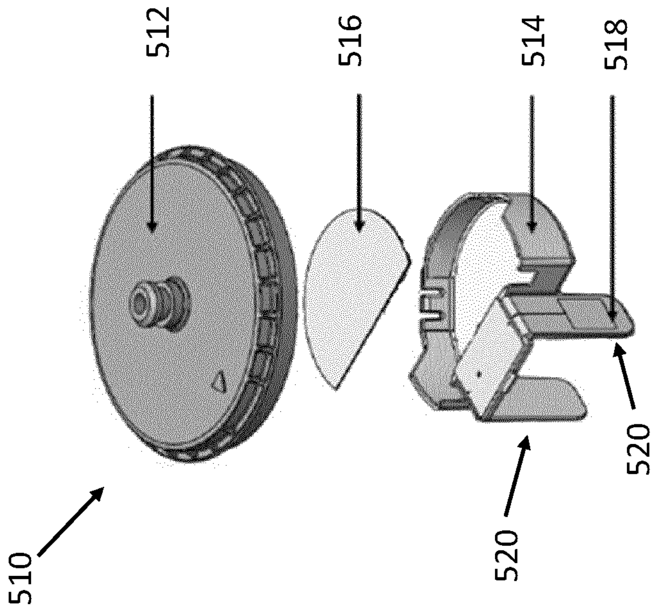
FIG. 5A illustrates an exploded view of a canister top and associated components.

Accordingly, it can be useful to have a more accurate detection method for detecting a full canister condition or a nearly full canister condition that reduces the nuisance alarms. The canister can have a canister detection system that allows for fluid detection that uses a device that communicates with fluid within the canister to detect when the fluid reaches a threshold level within the canister. The canister can incorporate the fluid level sensor device within a surface of the canister. For example, the canister can incorporate a fluid level detector (also referred to as a fluid level sensor) within a cap portion of the canister system. FIG. 5A illustrates a canister cap 510 that can be positioned on a surface of the canister configured to mate or be in a mating arrangement with the negative pressure wound therapy device, such as the pump assembly 160. The canister cap 510 can be positioned to provide fluid communication between the negative pressure source and the interior of the canister. For instance, the canister cap 510 can be positioned at the top of the canister 162, as is shown in FIG. 2A. The pump assembly 160 can be removably attached to the canister cap 510.

The canister cap 510 can include a housing formed from a cap top 512 and a cap bottom 514. The canister cap 510 can include a filter 516 positioned between the cap top 512 and the cap bottom 514. A fluid level sensor 518 can be included within the canister cap 510 to communicate with the interior of the canister. The fluid level sensor 518 can include two arms 520 that extend from the cap bottom 514 into the interior of the canister. The arms 520 can be made of conductive material (such as, conductive metal). The arms 520 can be used to interact with the fluid within the canister and create a completed circuit when the arms of the fluid level sensor 518 are in communication with fluid in the canister, which can thereby detect a canister full condition. The fluid level sensor can detect a completed electrical circuit when fluid within the interior of the canister is in contact with the arms of the fluid level sensor. For example, the fluid level sensor can detect fluid collection capacity within the canister when the circuit is open and a canister full condition when the circuit is closed. In other examples, the fluid level sensor can detect fluid collection capacity within the canister when the circuit is closed and a canister full condition when the circuit is open. A reader within the negative pressure wound therapy device can communicate with the fluid level sensor and, responsive to the canister full condition being detected, can provide an indication of a condition of the canister. The reader can also cause a change in the provision of negative pressure wound therapy (such as, cease application of negative pressure) or cause an alert (such as, a canister full alert) in response to the canister full condition being detected by the fluid level sensor. The reader can be positioned within a housing of the negative pressure wound therapy device, such as the pump assembly 160.

While the fluid level sensor 518 is shown with two downwardly extending arms, the fluid level sensor can include only one arm or any number of arms that extend into the interior of the canister to detect fluid within the canister. In some cases, the fluid level sensor can have any number or extensions or arms as long as at least two separate tracks of conductive material (or electrodes) are present to form the completed electrical circuit.

Figure 5B:
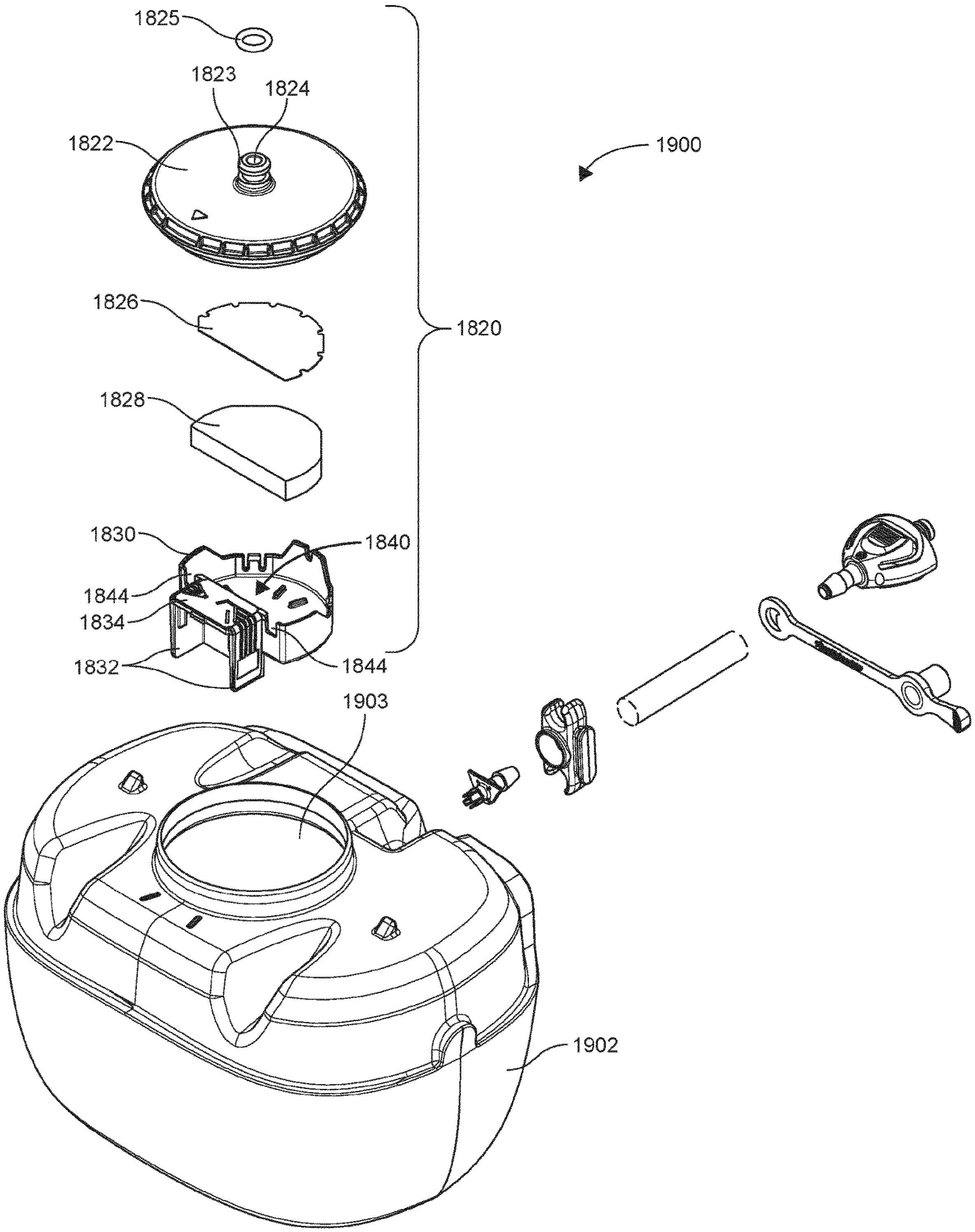
FIG. 5B-5E illustrates exploded views of a canister top and the pump assembly components.
Figure 5C:
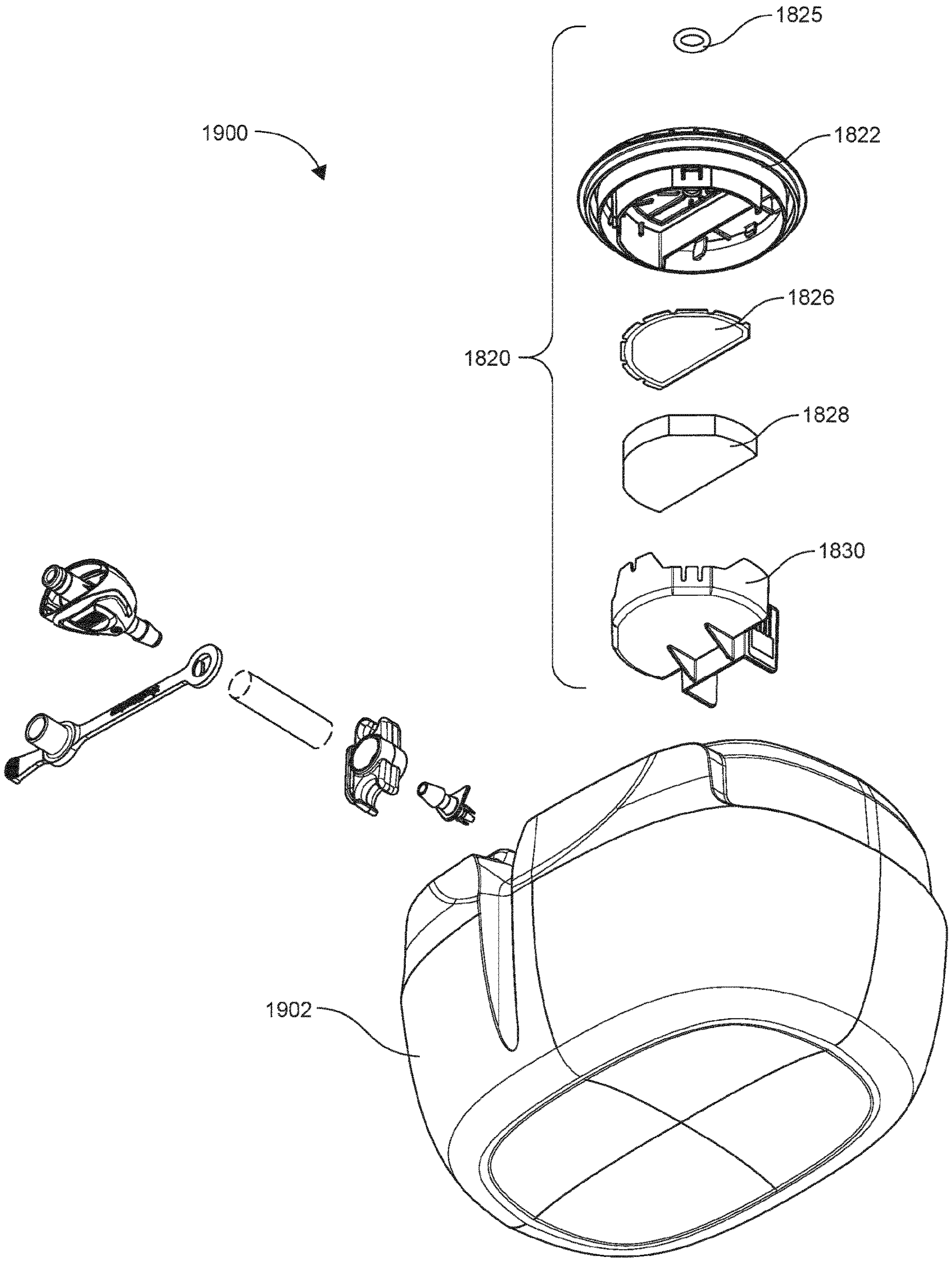

FIGS. 5B and 5C illustrate an exploded view of a canister cap assembly and the canister body or canister housing with a canister cap assembly 1820 similar to the canister cap and components described with reference to FIG. 5A. The canister cap assembly can be assembled and attached to the canister body which can then be coupled to pump assembly 160 or pump housing as shown in FIG. 2A. The cap assembly 1820 can be configured to be removably coupled (for example and without limitation, threadedly coupled) with an opening (such as 1903 shown in FIG. 5B) of the canister body 1902. In some arrangements, the cap assembly 1820 can be welded to the canister body 1902 or otherwise nonremovably coupled to the canister body. Some arrangements of the cap assembly 1820 can include a cover or first cap member 1822 having a connector interface 1823 that can have an opening 1824 extending axially through a center portion of the first cap member 1822. The connector interface 1823 can project axially away from a first main surface of the first cap member 1822. The connector interface 1823 can have a generally cylindrical shape and an annular flange formed thereon that can be configured to receive a seal, such as an O-ring 1825. The opening 1824 can be configured to provide a fluid passageway for air and/or other gases within the canister body 1902 to pass and to exit the canister body 1902 through.

The cap assembly 1820 can include an upper filter 1826 and an odor filter 1828. The upper filter 1826 can be a hydrophobic filter and/or a dust filter. The odor filter 1828 can also be configured to filter out bacteria from the air flowing through the filter 1828. The upper filter 1826 can be used to prevent any liquids from escaping from the canister body 1902 through the opening 1824 in the first cap member 1822 and can be positioned on either or both sides of the odor filter 1828. The odor filter 1828 can include any suitable filter membrane or material, including carbon. For example and without limitation, some arrangements of the odor filter 1828 can include compressed carbon.

The cap assembly 1820 can also include a base cap support 1830 that can be configured to provide a support surface for one or more of the filters 1826, 1828 and/or other components of the cap assembly 1820. The base cap support 1830 be configured to block or shield the one or more filters 1826, 1828 from exudate and/or other liquids within the canister. In some arrangements, the base cap support 1830 can have a main surface 1840 that can overlap or cover at least a portion of the filter 1828 so as to inhibit or prevent liquid or exudate within the canister 1902 from splashing onto at least a portion of the odor filter 1828 and/or the upper filter 1826. For example and without limitation, the main surface 1840 can overlap at least 80% of a surface area of a lower main surface of the odor filter 1828, or at least 90% of a surface area of the lower main surface of the filter 1828, or from at least 60% or approximately 60% to 90% or approximately 90% of a surface area of the first main surface of the filter 1828.

The base cap support 1830 can have one or more openings 1844 formed therein that air and/or other gases can pass through as the air and/or other gases are being drawn through the cap assembly 1820 when the pump is in operation. The cap assembly 1820 can be configured such that all air or gas or substantially all air or gas coming from the canister body 1802, 1902 must pass through the filter 1828 before passing through the opening 1844 in the cap assembly 1820. In some arrangements, there can be 3 or more, 4 or more, 5 or more openings 1844 formed in the base cap support 1830. The openings 1844 can be formed in walls that are perpendicular to a top main surface of the canister body 1802, 1902 so that exudate is less likely to splash or otherwise pass through the openings 1844—e.g., the openings 1844 can be formed in vertical walls of the base cap support 1830.

The cap assembly 1820 can include a fluid level sensor 1834 to detect the fluid level within the canister and/or if the canister is full or nearly full. The fluid level sensor 1834 can include two downwardly extending arms 1832. The fluid level sensor 1834 and arms 1832 can be similar to the fluid level sensor 518 and arms 520 described with reference to FIG. 5A.

Figure 5D:
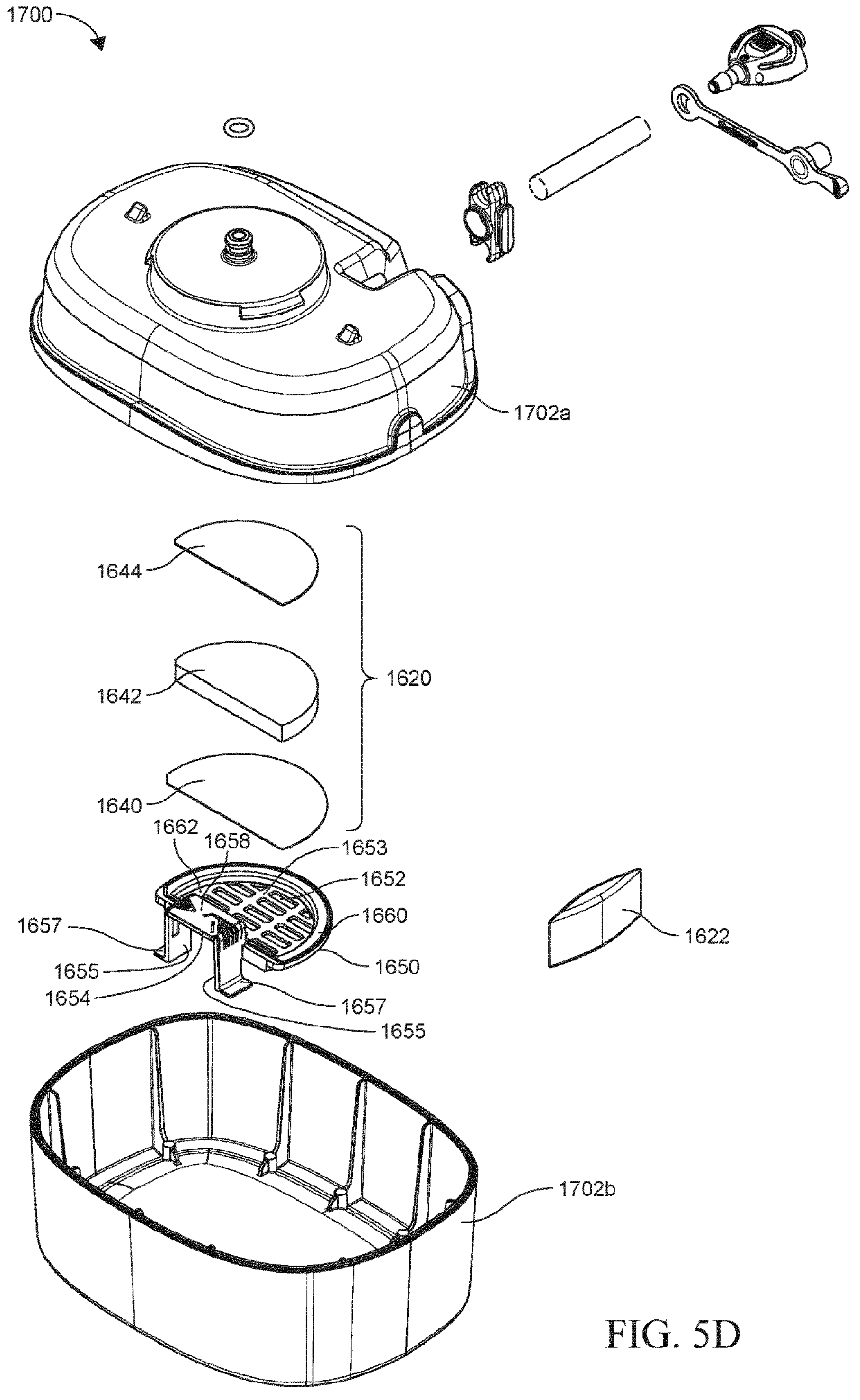
Figure 5E:
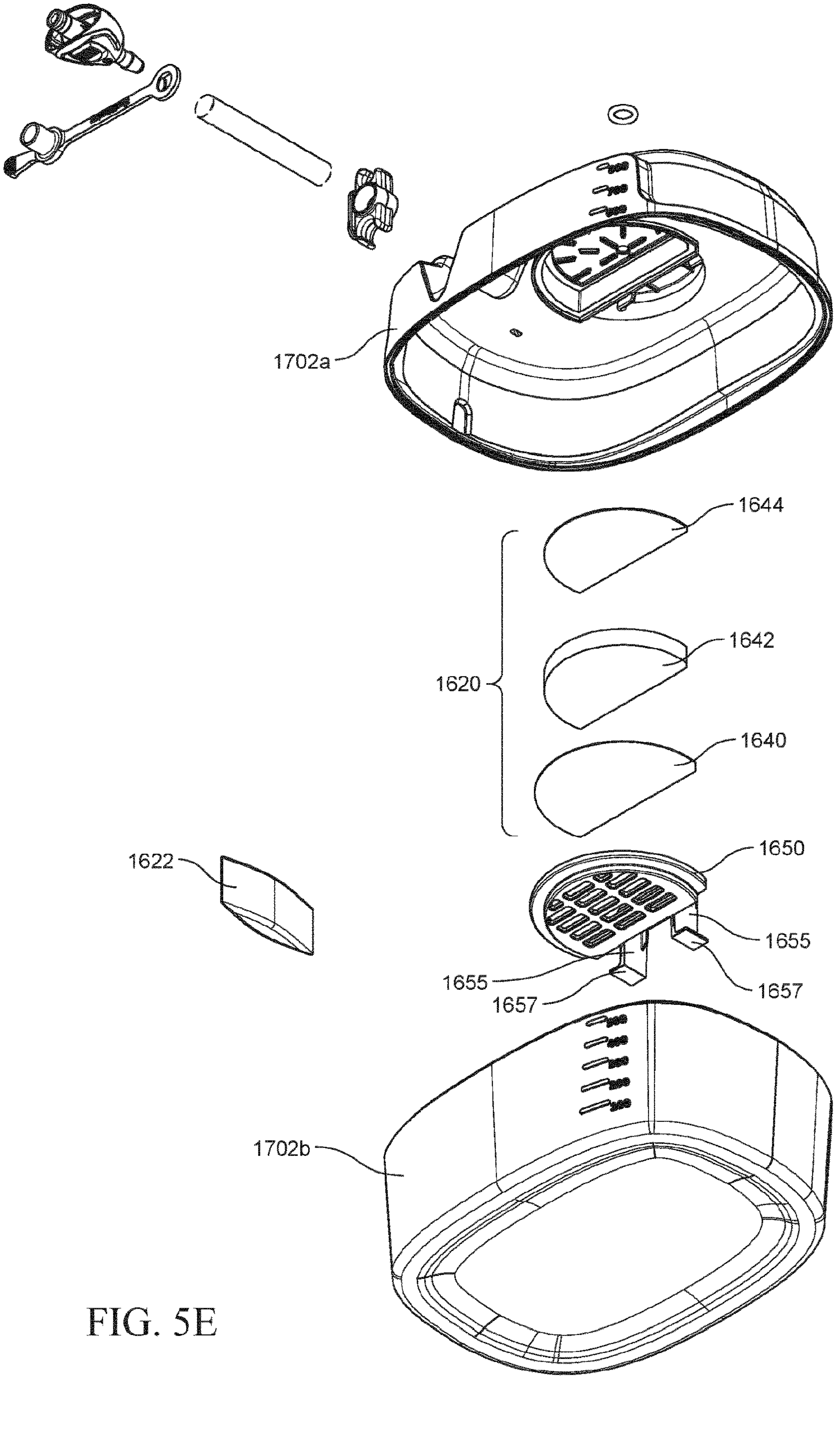

FIGS. 5D and 5E illustrate an exploded view of a canister assembly 1700. The canister assembly 1700 can have a canister body 1702 with a first body portion **1702*a* and a second body portion 1702*b*. The canister assembly can include a filter assembly 1620. The filter assembly 1702 can include a hydrophobic filter 1640, an odor filter 1642, and a dust filter 1644 that can be used to inhibit (e.g., prevent) dust or other particulates from passing through to the pump assembly. The odor filter 1642 can also be configured to filter out bacteria from the air flowing through the filter assembly 1620. The hydrophobic filter 1640 can be used to prevent any liquids from escaping from the canister body 1702 and from contacting the odor filter 1642. The odor filter 1642 can include any suitable filter membrane or material, including carbon. For example and without limitation, some arrangements of the odor filter 1642 can include compressed carbon. The filter assembly 1620 is also shown in FIGS. 5D and 5**E.

The filter assembly 1620 can be supported at a lower end or interior end by a base support 1650 that can be configured to provide a support surface for the hydrophobic filter 1640 and/or other components of the filter assembly 1620. The base support 1650 can have one or a plurality of openings 1652 through a main surface 1653 thereof through which air/or other gases can pass as air and/or other gases are being drawn by the pump through the filter assembly 1620.

Some arrangements of the base support 1650 can optionally be configured to support a sensor or sensors and/or other electronics components. With reference to FIG. 5D, some arrangements of the base support 1650 can have a support surface 1654 configured to support a sensor 1658 and/or other electronic components. For example and without limitation, the base support 1650 can have a support surface 1654 that is approximately parallel with a top surface of the canister assembly 1700. In some arrangements, the base support 1650 can also have one or more support tabs 1655 (two being shown) to provide additional support for a sensor or sensors and/or other electronics components. For example, the sensor can include a pair of electrodes configured to determine a fill level of the canister or detect that the canister is full responsive to a detection of electric current being conducted between the electrodes via liquid (e.g., wound exudate) aspirated into the canister as described herein. The support tabs 1655 can support the pair of electrodes, which can be positioned on the outward facing side of the support tabs 1655.

The support tabs 1655 can extend away from the support surface 1654 toward a bottom of the canister. The support tabs 1655 can have a flange or shield 1657 at a distal end of each of the support tabs 1655 to inhibit liquid (e.g., wound exudate) within the canister from splashing onto the support tabs 1655 and/or the electronics components 1658 (such as, electrodes) and from exposure to a gel packet 1622 or a mound of gelling agent. In some arrangements, the flanges 1657 can each extend at an angle (e.g., at a perpendicular angle) away from the support tabs 1655. In other arrangements, the flanges 1657 can extend at an angle that is greater than or less than 90 degrees relative to the support tabs 1655.

In some arrangements, the electronics components 1658 can optionally be a fill level sensor or a canister full sensor as described herein. For example, the fill level sensor can have a wireless transmitter thereon (that can optionally be a near field communication transmitter) that can be configured to communicate status information (such as, detected fill level or whether the canister is full) to a wireless receiver in the pump assembly or otherwise, or can have a wired connection through the canister in communication with the pump assembly. The flanges or shields 1657 can reduce or prevent fluid from splashing onto the fill level sensor or canister full sensor to prevent false detection. In some cases, the flanges or shields 1657 can be utilized to shield the electronics from the gelling agent bag or fluid solidifier within the canister. The fill level sensor or canister full sensor can be adhered to or otherwise fixed or attached to the support surface 1654 and/or the support tabs 1655. In other cases, the fill level sensor or canister full sensor can rest on at least a portion of the support surface 1654 and/or the support tabs 1655.

The base support 1650 can have an annular flange 1660 around a perimeter thereof and a recessed portion 1662 that can be configured to receive and support at least the hydrophobic filter 1640. The base support 1650 can be welded, adhered, or otherwise coupled within an inside surface of the first body portion **1702*a* of the canister body 1702 of the canister assembly 1700, optionally, before the first and second portions 1702*a*, 1702*b* of the body 1607** are coupled together.

The fill level sensor or canister full sensor can be overmoulded into the canister assembly. In other cases, the fill level sensor or canister full sensor can be insert moulded into the canister assembly. The fill level sensor or canister full sensor can be screen printed onto the canister assembly, for example, the electrical tracks can be screen printed onto the canister assembly. These techniques can be helpful during assembly and manufacture because these methods can eliminate the need to put the fill level sensor or canister full sensor into the canister. The fill level sensor or canister full sensor can be adhered to the support surface and/or the support tabs by ultrasonic welding or an adhesive. This method can take advantage of manufacturing methods for ultrasonic welding and adhesive application that are used for other components of the canister.

The fluid level sensor can include or be part of a detection system configured to communicate wired or wirelessly (such as, using NFC, RFID, etc.). The detection system can utilize fluid level sensor that incorporates a communication device to communicate information from the canister to the device or another remote computing device 334 (such as, the remote computing device 334). The detection system can utilize a communication device for communicating the information from the canister to the device using NFC. NFC is a set of short-range wireless technologies, typically requiring a separation of 10 cm or less (in some cases, 4 cm or less). NFC can involve an initiator (or active tag) and a target (or passive tag). The initiator can actively generate a radio frequency (RF) field that can power the passive tag. In some cases, NFC communication can utilize an NFC reader communicating with a passive NFC tag. The NFC reader can retrieve information stored in the passive NFC tag. The pump assembly 160 can include an NFC reader (which can be located at or near the bottom of the pump assembly 160 housing) and the detection system of the canister can include a passive NFC tag. When the conductive portions of the NFC tag are in contact with fluid within the canister and the circuit is closed, information (such as, a flag) can be stored in memory of the NFC tag. The NFC reader can read such information by communicating with the NFC tag. The NFC reader and NFC tag can include one or more antennas to facilitate wireless communication (for example, facilitate transmission and reception of data). In some cases, the range of communication between the NFC reader and the NFC tag can be about 20 mm (or less or more), which can exceed the distance between the NFC reader and the NFC tag. Additional details of utilizing NFC communication for determining canister status are disclosed in co-pending International Patent Application No. PCT/EP2022/060464 titled "COMMUNICATION SYSTEMS AND METHODS FOR NEGATIVE PRESSURE WOUND THERAPY DEVICES," filed on the same day as the present patent application, and incorporated by reference in its entirety.

As described herein, a negative pressure wound therapy device, such as the pump assembly 160, or a remote computing device can include an NFC reader. The NFC reader can have an antenna configured to facilitate communication with the canister, such as the canister 162. The pump assembly 160 can receive data relating to the status of the canister, such as whether the canister is full, the level of fluid in the canister, or the like. Additional approaches for communicating the with the pump assembly are disclosed in the above-referenced International Patent Application No. PCT/EP2022/060464 titled "COMMUNICATION SYSTEMS AND METHODS FOR NEGATIVE PRESSURE WOUND THERAPY DEVICES."

To detect the fluid level within the canister, the detection system can utilize a tamper detection system to detect when the fluid in the canister reaches a threshold level. The tamper detection system can detect a change in impedance or resistance in the circuit to determine if the system has been tampered with. For example, when used in packaging, detection of an open circuit in the tamper detection system can indicate tampering of the device such as the opening of a parcel. The fluid detection system can utilize the tamper detection system to detect canister full when the tamper detection system detects a closed circuit caused by the fluid level in the canister reaching (or exceeding) a threshold fluid level. Accordingly, the tamper detection system can detect canister full responsive to a closed circuit, which can be indicative of no tampering (rather than tampering detected with the open circuit as used in the case of packaging solutions).

Figure 6B:
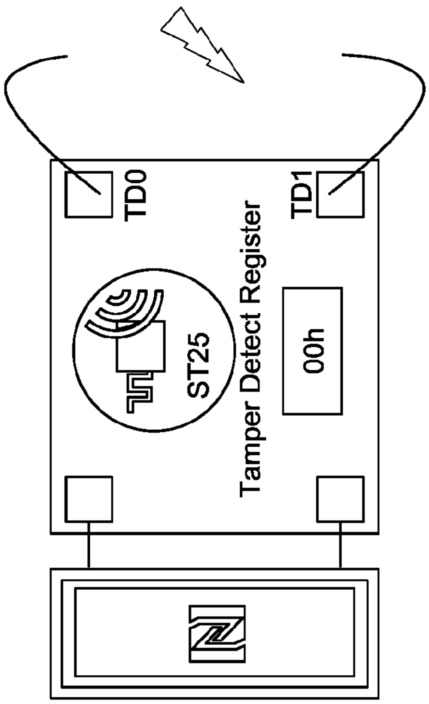
FIGS. 6A-6D illustrate a canister status detection system for a negative pressure wound therapy system.
Figure 6A:
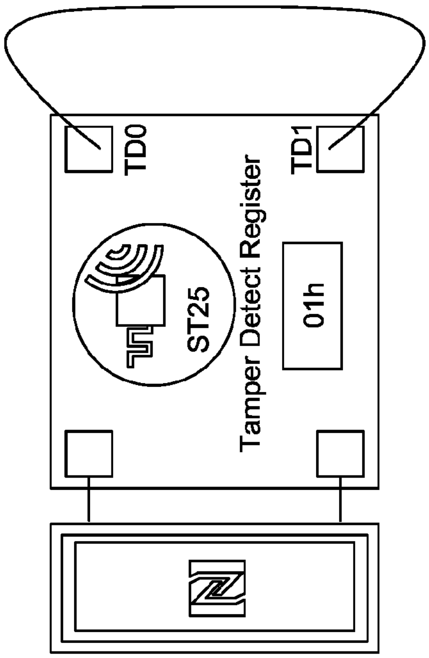

FIGS. 6A and 6B illustrates an example tamper detection system circuit and the state of tamper detection circuit. The illustrated tamper detection system can be configured to communicate using NFC (using an antenna illustrated on the left). FIG. 6A illustrates the tamper detection system in a "not tampered" state corresponding to a closed circuit state (in which nodes TD0 and TD1 are electrically connected). FIG. 6B illustrates the tamper detection system in a tampered state or open circuit state (in which nodes TD0 and TD1 are not electrically connected). The state of the system can be stored in a dedicated register. For instance, "01h" (or "1") can indicate closed circuit and "00h" (or "0") can indicate open circuit. The fluid within the canister can be used to close the circuit creating the not tampered state illustrated in FIG. 6A. When the tamper detection system is incorporated into a fluid detection system (such as, the fluid level sensor 518), the fluid detection system can have a first state that can be the 'canister empty' condition that corresponds to an open circuit (such as, 'tampered' as shown in FIG. 6B), and a second state can be a 'canister full' condition that corresponds to a closed circuit due to the fluid within the canister completing the circuit (such as, 'not tampered' as shown in FIG. 6A). For example, when fluid within the canister reaches a certain level, the arms 520 of the fluid level sensor 518 can be in contact with the fluid within the canister thereby completing the circuit and allowing the fluid level sensor to detect a canister full condition.

The tamper detection system can detect that the circuit is closed based on monitoring the impedance or resistance between nodes TD0 and TD1. In some cases, a threshold impedance for detecting a closed circuit should correspond to the impedance of the fluid (such as, wound exudate) expected to fill the canister. Testing of various fluids, including tap water, saturated salt water, and stimulated exudate (0.9% saline), has revealed impedances of about 460K, about 342, and about 662, respectively. The threshold impedance can be set to a value that equals or exceeds these impedances. For instance, the threshold impedance can be set to about 352 (or more), about 50K (or less or more), about 70K (or less or more), about 1002 (or less or more), about 0.5 kΩ (or less or more), about 1 kΩ (or less or more), about 2 kΩ (or less or more), about 3 kΩ (or less or more), about 4 kΩ (or less or more), about 5 kΩ (or less or more), about 6 kΩ (or less or more), or less than about 7.5 kΩ. In some cases, the threshold impedance can correspond to an average impedance of at least some of the fluids expected to fill the canister.

In some instances, the threshold impedance can be a preset value. The area of one or more of the electrodes of the fluid level sensor can be adjusted to ensure that the impedance of the closed circuit matches such present threshold impedance. For example, suppose that the preset threshold impedance is no more than 50K. In such case, the area of the one or more of the electrodes can be increased to ensure that closed circuit impedance does not exceed 50K.

In some cases, a reliable canister detection can be implemented. The fluid detection system can communicate an identifier, which can be a unique value (such as, a unique canister identifier). For instance, when NFC protocol is used (which operates over a short range), the negative pressure wound therapy device can be configured to disallow provision of therapy unless the identifier has been received from the canister (indicating that the canister has been attached to the device).

In some cases, the pump assembly can be used with canisters of various volumes or sizes. In such cases, the canisters of different volumes or sizes can be identified by changing the location (or number) of the fluid level sensor (for example, NFC tag) within the canister on the different types of fluid containment canister. For example, a canisters of a first size can have a fluid level sensor or NFC tag in a first location (such as the center top of the canister body) while a second canister of a second size can have a fluid level sensor or NFC tag positioned in a second location (such as the top side of the canister body). This can be identified by the reader on the pump assembly to indicate the type of canister that has been attached to the pump assembly, rather than reading a coded message on the sensor to determine the canister type. Additionally, using sensors positioned at different locations for canisters for determining the canister volumes or sizes can allow for identification of the canister type even if data written to the sensor is written incorrectly.

Figure 6D:
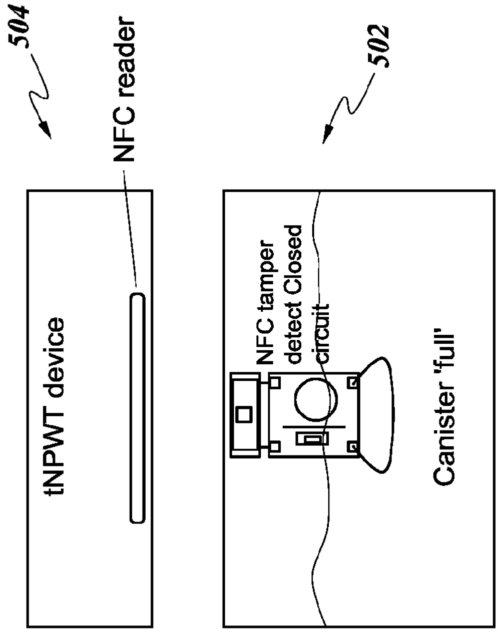
Figure 6C:
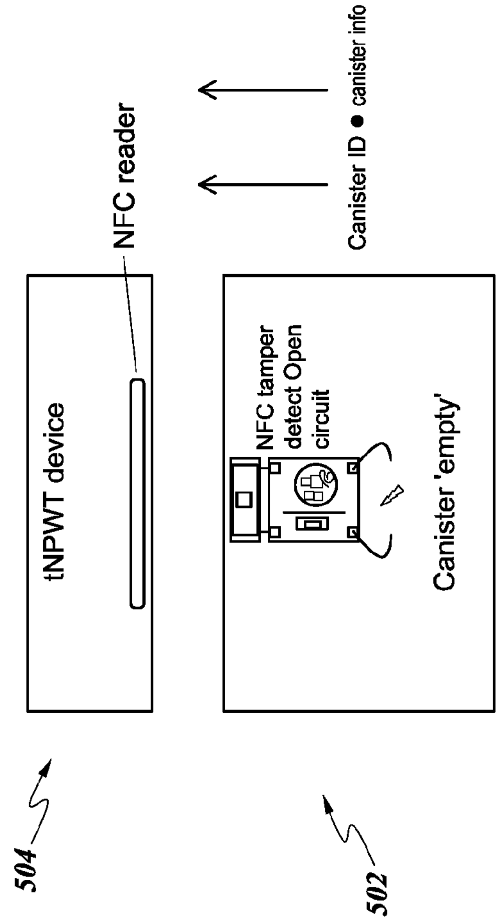

The state of the tamper detection system 502 that supports NFC communications (such as, functions as a passive NFC tag) can be detected with an NFC reader 504 as illustrated in FIG. 6C-6D. As described herein, the NFC reader 504 can be located within the negative pressure wound therapy device (labeled as "tNPWT device" in FIGS. 6A-6D), such as the pump assembly 160. Additional details about how the NFC reader can be integrated within the negative pressure wound therapy device are disclosed in the above-referenced International Patent Application PCT/EP2022/060464, titled "COMMUNICATION SYSTEMS AND METHODS FOR NEGATIVE PRESSURE WOUND THERAPY DEVICES."

In some cases, the tamper detection system can include memory that stores additional information related to the status of the canister. For example, the additional information may include information about the canister size (such as, 300 ml or 800 ml). In some cases, the additional information can include an indication whether the same canister had been previously attached to the negative pressure wound therapy device. For example, a unique canister identifier can indicate if the same canister is being removed and put back on the negative pressure system. The unique canister identifier can allow for tracking of the use of the canister. In some cases, the additional information stored in the tamper detection device in the canister can include tracking information entered into the device, such as the time and/or date when the canister was connected to the pump assembly, when the canister was removed from the pump assembly, and/or the number of hours of operating time. Additional details of the status of the canister are disclosed in International Patent Application No. PCT/EP2022/060459, titled "INTELLIGENT DISPOSABLE DEVICES FOR WOUND THERAPY AND TREATMENT," filed on the same day as the present patent application, and incorporated by reference in its entirety.

In some cases, the tamper detection system can be used in combination with other canister full detection methods. Using two or more redundant systems can promote accuracy. For example, the tamper detection system can be used in combination with using a peak-to-peak voltage measurement from pressure pulses to avoid false positive alarms from the peak-to-peak voltage measurement system. This can be particularly advantageous when estimating the fill rate of the canister. For example, in some cases, the peak-to-peak voltage measurements can give a crude indication of the fill level and therefore the flow rate of the wound drainage. The tamper detection system could be used to ensure the alarm will trigger when the canister is near a full level or is full. Further, a third check by the user could be implemented to increase accuracy of the system. This third check can consist of a user interface input of the canister level (for example, 'low', 'half-full', 'nearly full'). In some cases, the user interface can utilize buttons or other modes of user input, as described herein. For example, pictures or text can be used on the buttons (e.g. using three buttons with each corresponding to a certain fluid level—each with a picture and/or text).

The fluid detection system can include a fill level sensor or canister full sensor that includes multiple sets of electrode pairs. In some cases, the multiple sets of electrode pairs can be positioned on multiple arms. Additionally or alternatively, the fluid detection system can utilize multiple fill level sensors or canister full sensors (for example, multiple NFC tags) within the canister. For example, in some cases, rather than a single pair of arms or a single sensor extending into the canister as shown in FIG. 5A, multiple pairs of arms or multiple sensors can be used. Multiple pairs of arms or multiple sensors could be used with different lengths to measure a fluid level as the canister fills with liquid and before it becomes full or nearly full. In some cases, the sensor as described herein can include multiple pairs of arms at multiple distance from the canister top or cap. In some cases, multiple sensors can be used and stacked or positioned in an arrangement that allows for them to detect at different fill levels as the canister fills with liquid. This can allow for detection at various levels within the canister to allow the user to determine the amount of volume remaining the canister or to determine a fill rate of the canister as described herein.

For example, there can be three pairs of arms positioned at or extending into the canister body to different locations within the canister. A first pair of arms (longest pair of arms) can extend into the canister to a position the would indicate the canister is half filled with liquid. A second pair of arms can be shorter than the first pair but longer than the third pair and can extend into the canister to a position between a position that would indicate the canister is half filled and a position that would indicate the canister is full. A third pair of arms can be the shortest pair of arms and is positioned in a location that would indicate the canister is full or nearly full. If only the first pair of arms detect fluid, then the canister is half full. If the second pair of arms detect fluid then the canister can be $\frac{3}{4}^{th}$ of the way full or some volume between halfway full and full or nearly full. If the third pair of arms detect fluid, then the canister is full or nearly full. The multiple pairs of arms can also be used to measure a "time to full" of the canister as described further herein. The pairs of arms can be on the same sensor device (or same support substrate) or can be in the form of multiple sensors (for example, multiple NFC tags) each having pairs of arms and each pair of arms differs in length from another pair of arms. While three pairs of arms are described, any number of pairs of arms or any number of sensor devices can be used to detect any number of levels within the canister. The fill level resolution can be increased with more sensors or pairs of arms at various levels.

In some cases, multiple sensor devices can be positioned at the same distance from the filter in the canister top but in multiple axes. The multiple sensors can generate redundancy against failure of a tag. Multiple sensors also offer the capability to mount the sensors offset to generate a fill gauge. The spacing of the tag read paths to generate the fill gauge can be set to a fixed increment of fluid or in a spacing appropriate for an expected time increment (e.g. wider spaced towards the start or as the bottom of the canister fills to cope with a bolus of fluid delivered to the canister and then the tags can be more closely spaced later as it would be expected that the fluid rate tails off as the canister fills). The latter would give the greatest granularity of whether the wound is following an 'expected' path with the minimum number of track paths. In some cases, the multiple sensors or sensor with multiple arms can be set at different lateral positions within the canister.

Figure 6E:
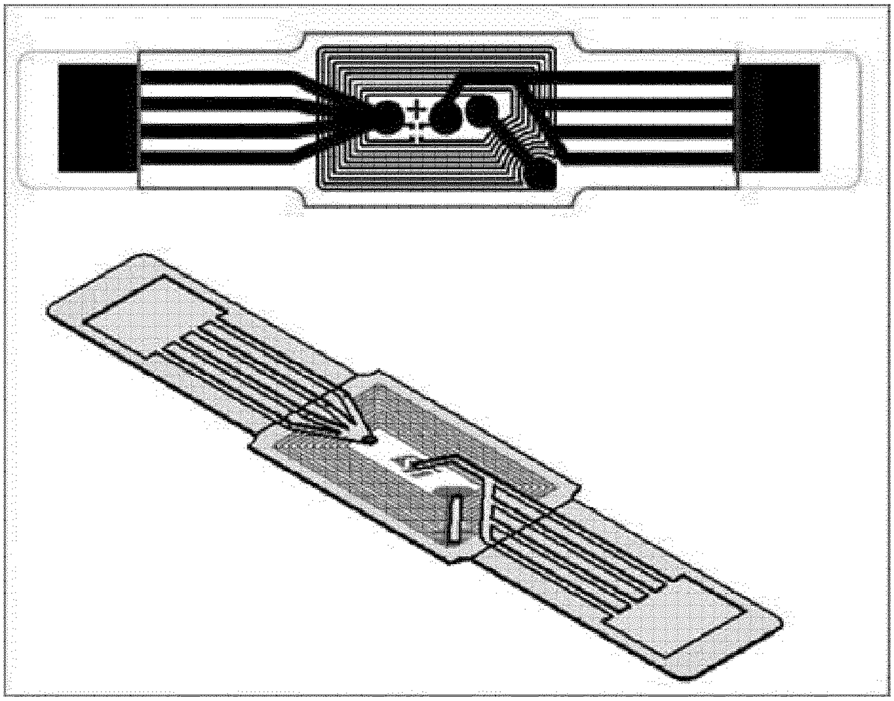
FIG. 6E illustrates multiple views of a fluid level sensor.

FIG. 6E illustrates an NFC tag that can be used as a fill level sensor assembly. The NFC tag can be used for detecting the fluid level within the canister as described herein. The canister can be a critical portion of the negative pressure therapy. In some cases, pump assembly cannot perform patient negative pressure therapy without the canister present. The canister must be pneumatically connected and attached to the pump assembly and/or a wound dressing.

Any of the canister cap embodiments described herein can contain the NFC tag fill level sensor assembly as shown in FIG. 6E. In some cases, as described herein, the short-range wireless NFC communication can validate the attachment of the canister to the pump assembly and validate that the canister is attached properly. The main function of the canister's NFC tag fill level sensor assembly is to allow the passive NFC device within the canister to wirelessly communicate to the NFC reader located in the pump assembly. The wireless function of the NFC tag sensor assembly can transmit data relating to canister detection, fluid detection, and programmed canister data. The NFC tag device illustrated in FIG. 6E includes the tamper-proof feature described here. In some cases, the NFC tag device can include specific modes to protect tag access, such as an untraceable mode. In some cases, the NFC device can include a digital signature used to prove the origin of the chip in cloning detection, embed a configurable EEPROM with 60-year data retention, and/or can be operated from a 13.56 MHz long-range RFID reader.

Canister Fill Rate Detection

It can be advantageous to detect and indicate the fill rate of a canister, such as the canister 162, in the negative pressure system. This detection can be performed in addition to or as an alternative to the canister full or near full detection described herein.

The canister fill rate can be used to infer the wound drainage or how much exudate is flowing out of the wound. The flow rate of fluid from the wound can be calculated using the time taken to fill the canister based on the duration of time between an empty canister being installed and the time canister full is detected. The volume of the canister can then be divided by the time taken to fill the canister to calculate the flow rate of wound fluid. For example, the following equation can be used:

$$\text{flow rate}=(\text{canister volume})/(\text{time taken to fill}) \quad (1)$$

In some cases, the volume of the canister can be input by the user or can be detected (such as, retrieved from the memory of the canister as described herein). An accurate flow rate can be calculated using the fluid level sensor described herein. Time duration for filling the canister can be accurately determined by taking into account any stoppages or pausing of therapy, determination that the same canister is still attached there when therapy is resumed, and determination that the canister has been removed and reapplied. As described herein, these determinations can be made using the unique canister identifier.

In some cases, the flow rate can then be used by the healthcare provider to determine the best route of care and if the patient can be moved to another system, for example a Pico Single Use Negative Pressure Wound Therapy System from Smith & Nephew.

In some cases, the canister can be removed before the canister is full. In these situations, an inference can be made about the flow rate by providing a manual input to the user interface to state the level of fluid within the canister. In some cases, this input could be an input noting: 'low', 'half-full', 'nearly full', if the canister is removed before the canister is full or before the canister full alarm is triggered. This input can be used to adjust the canister volume variable in Equation 1.

In some cases, the information obtained from the canister, the canister fill rate, and/or canister use and therapy use can provide information to the healthcare practitioner and to allow for an understanding of trends and behaviors for a single patient or among various patients to assist in making healthcare decisions.

In some cases, a flow meter can be positioned in the fluid flow path (such as, in the conduit 108 or 108') to determine the flow rate. For example, a venturi tube can be used.

Inductively Coupled Fluid Detection System

A canister full detection system can use an inductively coupled fluid detection system. The inductively coupled fluid detection system can detect a full or nearly full canister and consequently provide an alert to the user. As described herein, the canister full or nearly full alert can be important for a negative pressure therapy system because it can allow a healthcare professional or a user to replace the canister and continue therapy with the least amount of interruptions (such as, not having to worry about the device suddenly sounding a canister full/blockage alarm).

Figure 7:
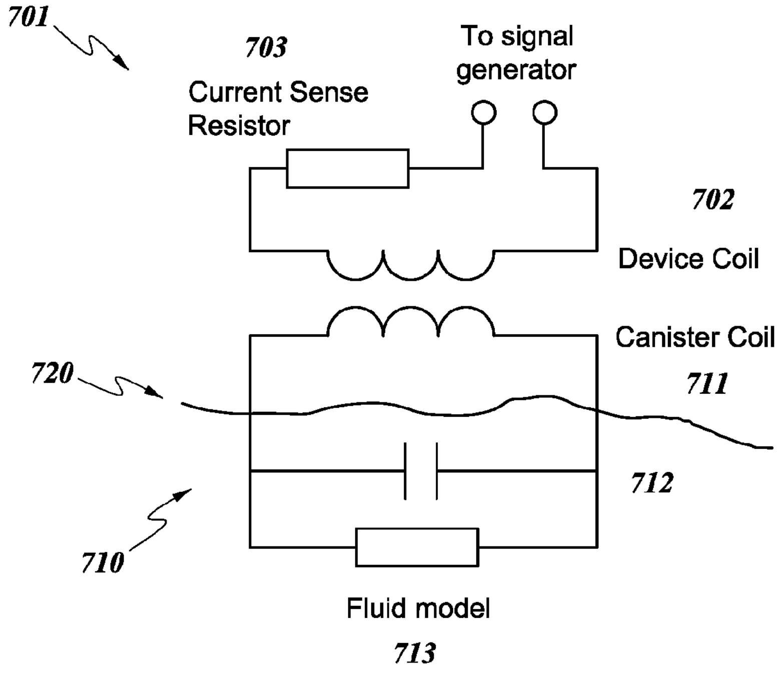
FIG. 7 illustrates a schematic diagram of a general circuit arrangement of an inductively coupled fluid detection system.

The negative pressure wound therapy system can use an inductively coupled fluid detection system to determine if the canister is near full. To do this, the system can use spaced-apart electrodes in the canister, which can detect fluid presence by the change in electrical properties when the fluid within the canister is at a certain level and the electrodes are submerged. The canister fluid level information can then be relayed back to the negative pressure therapy system, for instance, through inductive coupling (such as, NFC) or another wireless or wired communications protocol. For example, the inductively coupled fluid detection system can include one coil in a device (device side) and the other coil in the canister (canister side) as shown in FIG. 7. In some cases, this configuration can provide isolation by avoiding direct electrical connections between a canister, a device, and ultimately the user. The device side coil can be positioned at the bottom portion of the housing of the negative pressure wound therapy device, as described in the above-referenced International Patent Application PCT/EP2022/060464, titled "COMMUNICATION SYSTEMS AND METHODS FOR NEGATIVE PRESSURE WOUND THERAPY DEVICES."

FIG. 7 illustrates a schematic diagram of the general circuit arrangement of an inductively coupled fluid detection system. As illustrated in FIG. 7, a device side 701 of the inductively coupled fluid detection system can include a device coil 702 and a current sense resistor 703. The device side 701 can transmit to a controller of the negative pressure wound therapy device or to a connected or remote device information obtained by the detection system, for example, the canister full or canister nearly full condition. The canister side 710 of the inductively coupled fluid detection system can include a canister coil 711. The electrical properties of fluid in the canister (shown by the line 720) can be represented by a capacitor 712 and resistor 713. The coil 711 can be in electrical communication with the fluid via the spaced-apart electrodes.

In some cases, the coils 702 and 711 can be inductively coupled and information (in the form of electric current) can be relayed between the coils. The configuration with one coil in the device and the other in the canister can be ideal as it provides isolation by avoiding direct electrical connections between a canister, a device and ultimately the user.

Figure 8:
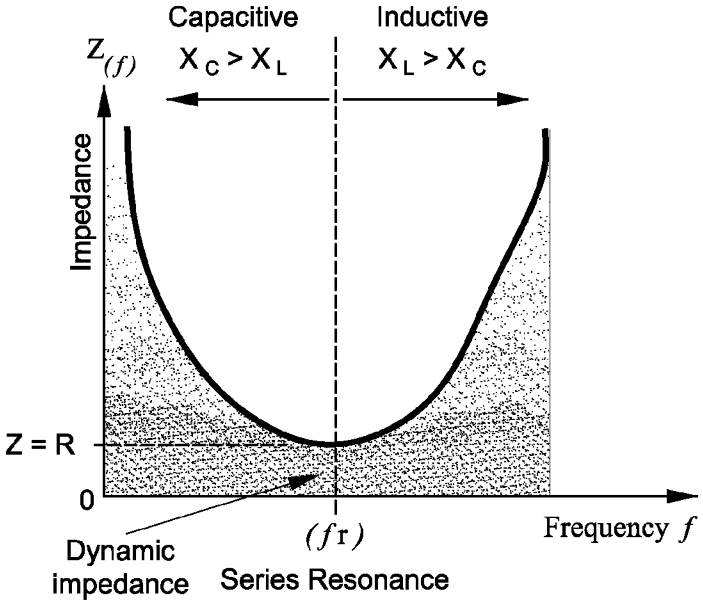
FIG. 8 illustrates a graph of impedance as a function of frequency.

The device coil 702 can be excited by an alternating current (A.C.) signal of a certain frequency. The canister coil 711 and the fluid in the canister can form a LC circuit that includes the coil 711 (inductor) and the capacitor 712, which represents the capacitance of the fluid. The impedance (or the effective opposition to the alternating current) of the capacitor 712 decreases as frequency increases. The impedance of the inductor 711 increases as the frequency increases, as shown in FIG. 8. The point at which both lines intersect is the series resonance (or resonant frequency), where the impedance is at its lowest and the highest current can flow. Therefore, with the alternating current at the resonant frequency signal being fed into the circuit, as a fluid is introduced into the canister and reaches the electrodes, the LC circuit can be completed. Completion of the circuit can introduce the capacitance 712, causing the impedance of the LC circuit to reach its lowest point and causing the current to be at its highest.

Figure 9A:
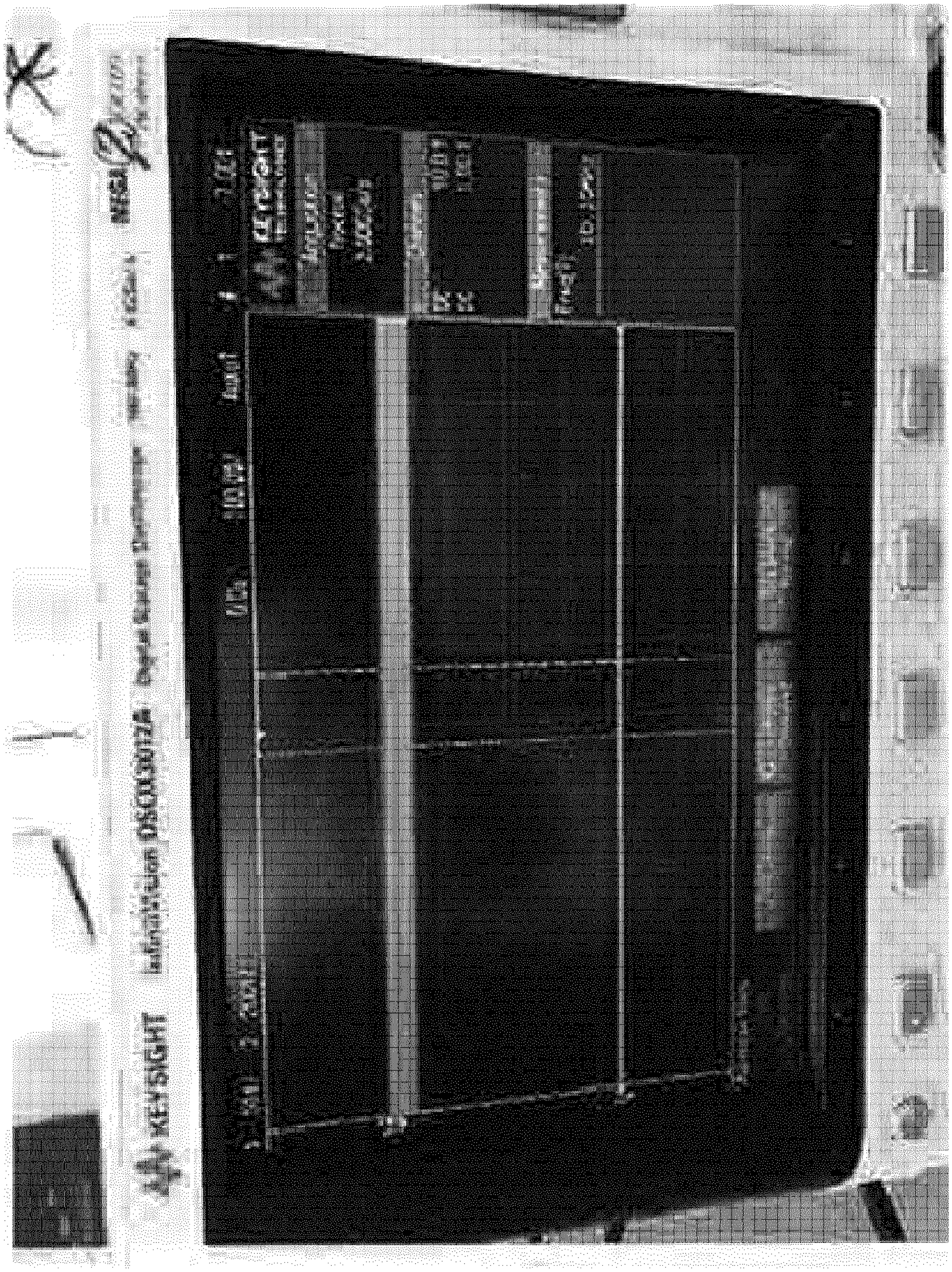
FIGS. 9A-9B illustrates example oscilloscope plots.
Figure 9B:
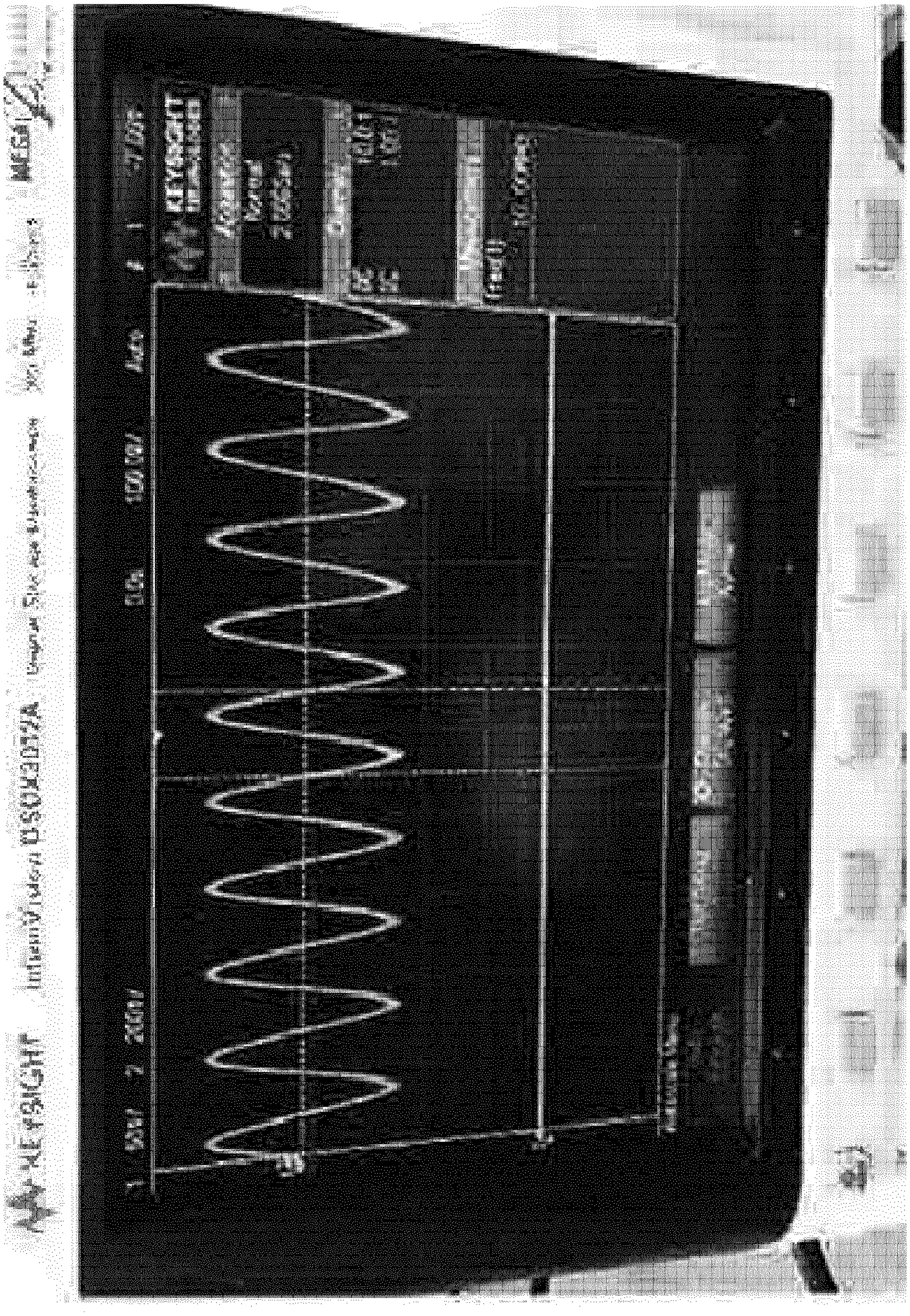

When the device coil 702 is inductively coupled to the canister coil 711, alternating current is coupled between two circuits. When there is no fluid within the canister (or the fluid has not reached the electrodes), the canister coil is in an open circuit and no current is flowing through the canister coil. This can cause very little current to flow though the device coil as shown in FIG. 9A, which illustrates an example of an oscilloscope plot measured when there is no fluid of the canister (or the fluid has not reached the electrodes). However, when fluid is aspirated into the canister (and the fluid reaches the electrodes), current induced by the device coil 702 starts flowing through the canister coil 711. In turn, this can increase the current flowing through the device coil 702. This current can be measured across the sense resistor 703 and compared to a threshold indicative of the canister being full. FIG. 9B illustrates an example of an oscilloscope plot measured when fluid in the canister has reached the electrodes. FIG. 9B illustrates larger current flowing through the device coil 702 as compared to FIG. 9A.

Figure 10:
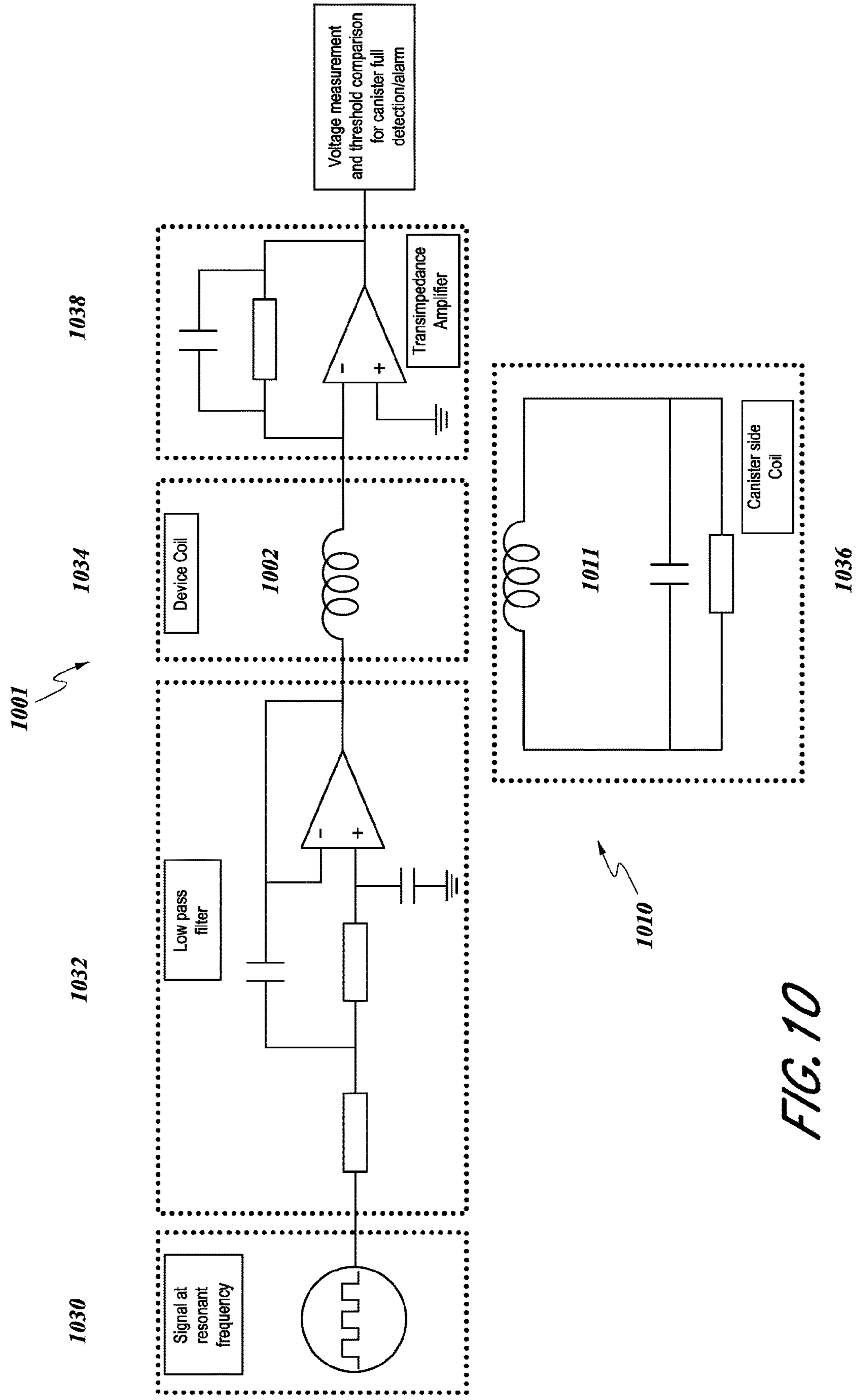
FIG. 10 illustrates a schematic diagram of an example circuit of an inductively coupled fluid detection system.

FIG. 10 illustrates a schematic diagram of an example circuit of an inductively coupled fluid detection system with signal manipulation for a canister full detection with the different sections involved. As shown in FIG. 10, in section 1030 a pulse signal waveform at the resonant frequency is generated (such as, by a microcontroller), and passed through a low-pass filter (LPF) to convert the signal into an alternating current signal at a corresponding fundamental frequency (such as, sine wave) in section 1032. This is achieved since the digital pulse (for example, a square wave or a PWM signal at 50% duty cycle) is composed of many frequencies and by filtering frequencies other than the fundamental frequency (in this case the resonant frequency is selected), a sine wave is generated. In some cases, the LPF can be a 2nd order Butterworth-type low-pass filter. In some cases, odd harmonics such as 3rd, $5^{th}$, or others may still remain, due to the −40 dB/decade drop-off of a 2nd order LPF, but the impedance from the device coil can attenuate those harmonics with a selection of components (such as, capacitors and resistors).

An inductively coupled fluid detection system can include a device side 1001 with a device coil 1002 shown in section 1034 and a canister side 1010 with a canister coil 1011 shown in section 1036. The device side 1001 and the canister side 1010 can be similar to the device side 701 and canister side 710 described with reference to FIG. 7 and can include the same components described with reference to FIG. 7. The alternating current signal at the resonant frequency can pass from the LPF in section 1032 to the device side 1001 of the inductively coupled fluid detection system in section 1034 as the current passes through the device coil 1002. The canister coil 1011 of the canister side 1010 of the inductively coupled fluid detection system can generate a current with the device coil 1002 when the circuit is complete, as described herein. For example, once the fluid reaches a threshold level in the canister (such as, reaches the electrodes), the circuit is complete and current is conducted across the canister coil 1011. As described in connection with FIG. 7, this current can cause the current across the device coil 1002 to change (such as, increase). This change can be detected, causing detection of the canister being full.

A transimpedance amplifier in section 1038 can be used to convert the current into a voltage which can then be interpreted more easily by the MCU or similar device. A comparison can be conducted between the output voltage generated from the transimpedance amplifier in section 1038 and a threshold value indicative of the canister being full. The comparison can be conducted with the condition that if the threshold value is satisfied (such as, reached or exceeded), a full canister has been achieved. Once it has been established that a full canister has been achieved an alarm can be triggered.

Figure 11:
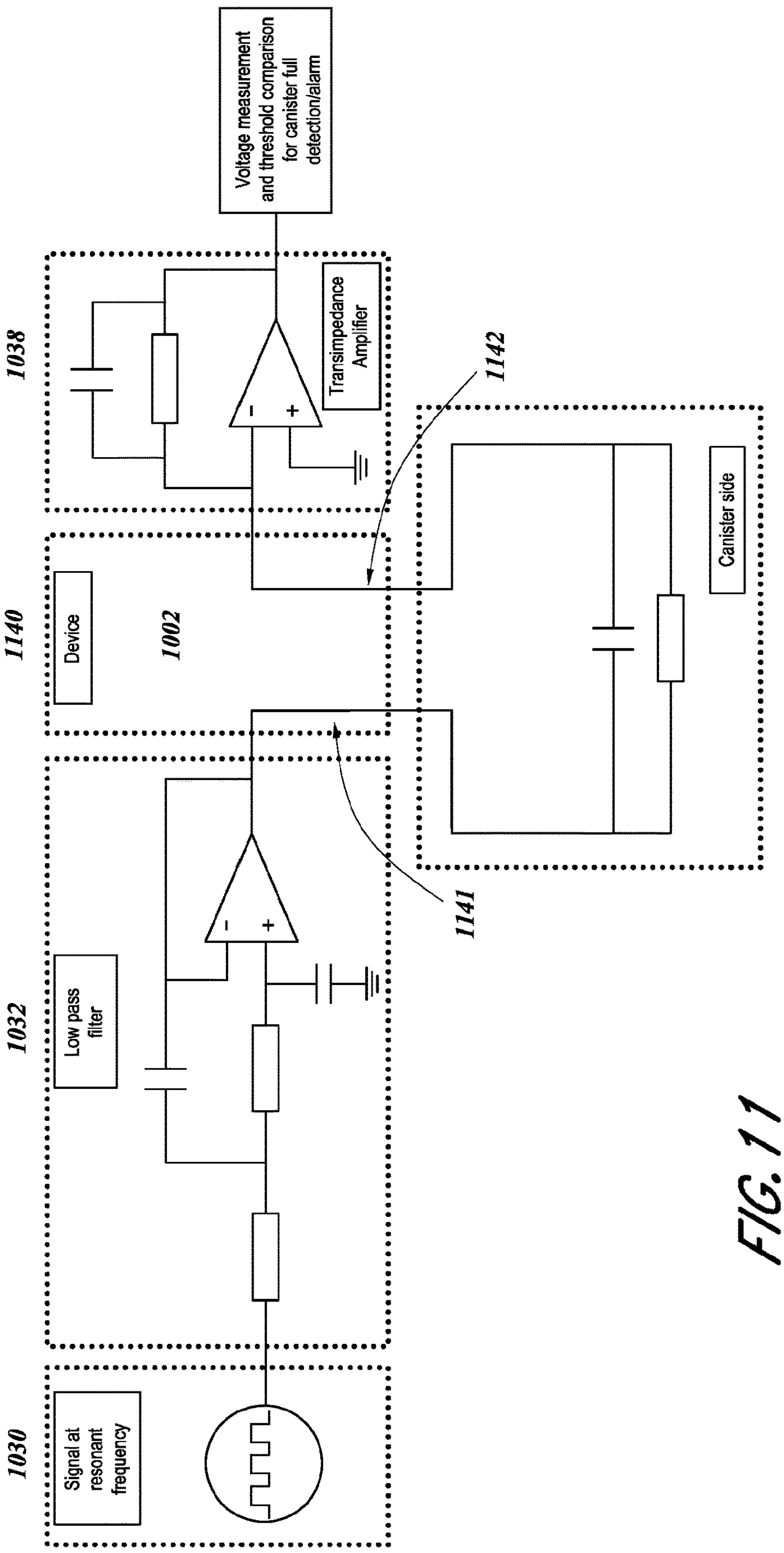
FIG. 11 a schematic diagram of an example circuit of a fluid detection system using direct connections into a canister.

FIG. 11 a schematic diagram of an example circuit of a fluid detection system using direct connections into a canister. The mechanism for canister full or near full detection can be similar to the inductively coupled fluid detection system described with reference to FIG. 10 but the fluid detection system described with reference to FIG. 11 uses electrical connections 1141, 1142 through the canister directly in section 1140 instead of using inductively coupled coils. The other section involved in the circuit described with reference to FIG. 10 are similarly involved in the circuit of FIG. 11. The use of the electrical connections may require an electrical interface to connect the canister and the device. The canister full detection can allow for a direct measurement as the electrical connections pass through the canister directly. Directly measuring the presence of fluid (via electrical properties of the fluid in the canister) can increase the robustness of the system by providing a direct way to measure and warn the user of a canister being full. A contactless device for measuring or detecting the presence of fluid can be electrically more robust and beneficial in some circumstances than a direct electrical connections system since it can avoid contamination problems. In other cases, a contactless system for measuring or detecting the presence of fluid can be more prone to RF interference and/or noise pickup.

In some cases, having direct electrical connections from the negative pressure wound therapy device though the canister interface may be undesirable (for instance, for patient safety). As a result, using the isolated inductively coupled circuit of FIG. 7 or 10 can be a more desirable solution to measure or detect that the canister is full.

While canister full detection is described in this section, detection of the canister being nearly full can be similarly performed.

Other Variations

Although some embodiments describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can in addition provide TNP therapy. The systems and methods disclosed herein are not limited to medical devices and can be utilized by any electronic device.

Any of transmission of data described herein can be performed securely. For example, one or more of encryption, https protocol, secure VPN connection, error checking, confirmation of delivery, or the like can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, “can,” “could”, “might,” “may,” “e.g.,” and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms “comprising,” “including,” “having,” and the like are synonymous and are used inclusively, in an open-ended fashion, and do not exclude additional elements, features, acts, operations, and so forth. Also, the term “or” is used in its inclusive sense (and not in its exclusive sense) so that when used, for example, to connect a list of elements, the term “or” means one, some, or all of the elements in the list. Further, the term “each,” as used herein, in addition to having its ordinary meaning, can mean any subset of a set of elements to which the term “each” is applied. Additionally, the words “herein,” “above,” “below,” and words of similar import, when used in this application, refer to this application as a whole and not to any particular portions of this application.

Conjunctive language, such as the phrase “at least one of X, Y and Z,” unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms “approximately,” “about,” “generally,” and “substantially” as used herein represent a value, amount, or characteristic close to the stated value, amount, or characteristic that still performs a desired function or achieves a desired result. For example, the terms “approximately”, “about”, “generally,” and “substantially” may refer to an amount that is within less than 10% of, within less than 5% of, within less than 1% of, within less than 0.1% of, and within less than 0.01% of the stated amount. As another example, in certain embodiments, the terms “generally parallel” and “substantially parallel” refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as “a” or “an” should generally be interpreted to include one or more described items. Accordingly, phrases such as “a device configured to” are intended to include one or more recited devices. Such one or more recited devices can also be collectively configured to carry out the stated recitations.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy device comprising:
- a device housing;
- a negative pressure source supported by the device housing, the negative pressure source configured to provide negative pressure to a wound covered by a wound dressing;
- a canister configured to be in fluid communication with the negative pressure source and the wound dressing, the canister comprising:
  - a canister housing comprising a first body portion and a second body portion, and configured to store fluid aspirated from the wound;
  - a base support positioned inside the canister housing and comprising a filter support portion and one or more support tabs, wherein the base support is connected to the first body portion of the canister housing, and wherein the first body portion is configured to be connected to the device housing when the canister is removably attached to the device housing;
  - a fluid level sensor supported by the one or more support tabs of the base support, the fluid level sensor comprising a pair of arms extending into an interior of the canister housing and configured to be in fluid communication with fluid aspirated from the wound, wherein the fluid level sensor is configured to detect a completed electrical circuit when the fluid aspirated from the wound comes into contact with the pair of arms of the fluid level sensor, and wherein the fluid level sensor is configured to detect a canister full condition when the electrical circuit is completed; and an electronic circuitry configured to detect a state of the fluid level sensor and provide an indication of a status of the canister; and
- a filter assembly supported by the filter support portion of the base support.

2. The negative pressure wound therapy device of claim 1, wherein the status of the canister comprises the canister full condition.

3. The negative pressure wound therapy device of claim 1, wherein the electronic circuitry is supported by the device housing.

4. The negative pressure wound therapy device of claim 1, wherein the fluid level sensor is configured to communicate with the electronic circuitry using Near Field Communication (NFC).

5. The negative pressure wound therapy device of claim 1, wherein the fluid level sensor comprises a Near Field Communication (NFC) tamper detection circuitry, and wherein responsive to the fluid aspirated from the wound completing a circuit in the NFC tamper detection circuitry, the fluid level sensor is configured to detect the canister full condition.

6. The negative pressure wound therapy device of claim 5, wherein the electronic circuitry comprises an antenna configured to communicate with the NFC tamper detection circuitry and facilitate transmission and reception of data.

* * * * *